United States Patent [19]
Galili et al.

[11] Patent Number: 5,367,110
[45] Date of Patent: Nov. 22, 1994

[54] TRANSGENIC PLANTS OVERPRODUCING THREONINE AND LYSINE

[75] Inventors: Gad Galili, Rehovot; Orit Shaul, Petah Tivka; Avihai Perl, Rishon-le-Zion, all of Israel

[73] Assignee: Yeda Research and Development Co. Ltd., Rehovot, Israel

[21] Appl. No.: 792,466

[22] Filed: Nov. 13, 1991

[30] Foreign Application Priority Data

Nov. 13, 1990 [IL] Israel .................................. 96340
Jun. 27, 1991 [IL] Israel .................................. 98650
Jul. 30, 1991 [IL] Israel .................................. 99014

[51] Int. Cl.⁵ .................. A01H 1/04; C12P 21/04; C12P 13/08; C12N 9/12
[52] U.S. Cl. ....................... 800/205; 435/115; 435/69.8; 435/70.1; 435/194
[58] Field of Search ............... 800/205; 435/172.3, 435/320.1, 240.4, 240.49, 240.5, 240.51, 115, 69.8, 70.1, 194; 424/405; 47/58

[56] References Cited

FOREIGN PATENT DOCUMENTS

3823451 1/1990 Germany .
8911789 12/1989 WIPO .

OTHER PUBLICATIONS

Bright, S. W. J., et al., *Nature*, vol. 299, pp. 287-79 (1982) (Exhibit D).
Cattoir-Reynaerts, A., et al., *Biochem. Physoil. Pflazen*, vol. 178, pp. 81-90 (1983) (Exhibit E).
Negrutiu, I., et al., *Theor. Appl. Genet.*, vol. 68, pp. 11-20 (1984) (Exhibit F).
T. Diedrick et al. *Theor. Appl. Genet.*, vol. 79 (1990) pp. 209-215.
S. Dotson et al., *Plant Physiology*, vol. 93 (1990) pp. 98-104.
R. Abersold et al. *P.N.A.S.*, vol. 84 (1987) pp. 6970-6974.
S. Gould et al. *P.N.A.S.*, vol. 86 (1989).
R. Schocher et al. *Bio/Technology*, vol. 4 (1986) pp. 1093-1096.
R. Horsch. et al. *Science*, vol. 223 (1984) pp. 496-498.
M. Cassan et al. *J. Biol. Chem.*, vol. 261 (1986) pp. 1052-1057.
P. Truffa-Bachi et al. *Biochem. Biophys. Acta*, vol. 113 (1966) pp. 531-541.

*Primary Examiner*—David T. Fox
*Assistant Examiner*—Charles Rories
*Attorney, Agent, or Firm*—John P. White

[57] ABSTRACT

A chimeric gene construct comprising a DNA sequence encoding an enzyme having aspartate kinase (AK) activity is provided, which is capable of expression in plant cells with subsequent increased production of threonine. Transgenic plants containing in their cells said chimeric gene overproduce threonine and transgenic plants containing in their cells said chimeric gene and a second chimeric gene comprising a DNA sequence coding for an enzyme having dihydrodipicolinate synthase (DHPS) activity, overproduce both threonine and lysine. The transgenic plants are resistant to lysine and threonine, to derivatives thereof and to selective inhibitors of the plant enzymes DHPS or AK, and thus these compounds may be used as selective herbicides in locus where the transgenic plants are cultivated.

1 Claim, 31 Drawing Sheets

FIGURE 3A

OMEGA SEQUENCE tattttacaacaattaccaacaacaacaaacaacaaacaacattacaattactatttaca
attaca

FIGURE 3B

PEA-*rbcS* TRANSIT PEPTIDE SEQUENCE tctagaaaaATGGCTTCTATGATATCCTCTTCCGCTGTGACAACAGTCAGCC
GTGCCTCTAGGGGGCAATCCGCCGCAGTGGCTCCATTCGGCGGCCTCAAA
TCCATGACTGGATTCCCAGTGAAGAAGGTCAACACTGACATTACTTCCA
TTACAAGCAATGGTGGAAGAGTAAAGTGCATGC

FIGURE 3C dapA SEQUENCE

ATGTTCACGGGAAGTATTGTCGCGATTGTTACTCCGATGGATGAAAAAGG
TAATGTCTGTCGGGCTAGCTTGAAAAAACTGATTGATTATCATGTCGCCA
GCGGTACTTCGGCGATCGTTTCTGTTGGCACCACTGGCGAGTCCGCTACCT
TAAATCATGACGAACATGCTGATGTGGTGATGATGACGCTGGATCTGGCT
GATGGGCGCATTCCGGTAATTGCCGGGACCGGCGCTAACGCTACTGCGGA
AGCCATTAGCCTGACGCAGCGCTTCAATGACAGTGGTATCGTCGGCTGCC
TGACGGTAACCCCTTACTACAATCGTCCGTCGCAAGAAGGTTTGTATCAG
CATTTCAAAGCCATCGCTGAGCATACTGACCTGCCGCAAATTCTGTATA
ATGTGCCGTCCCGTACTGGCTGCGATCTGCTCCCGGAAACGGTGGGCCGTC
TGGCGAAAGTAAAAAATATTATCGGAATCAAAGAGGCAACAGGGAACTT
AACGCGTGTAAACCAGATCAAAGAGCTGGTTTCAGATGATTTTGTTCTGC
TGAGCGGCGATGATGCGAGCGCGCTGGACTTCATGCAATTGGGCGGTCAT
GGGGTTATTTCCGTTACGACTAACGTCGCAGCGCGTGATATGGCCCAGAT
GTGCAAACTGGCAGCAGAAGAACATTTTGCCGAGGCACGCGTTATTAAT
CAGCGTCTGATGCCATTACACAACAAACTATTTGTCGAACCCAATCCAA
TCCCGGTGAAATGGGCATGTAAGGAACTGGGTCTTGTGGCGACCGATACG
CTGCGCCTGCCAATGACACCAATCACCGACAGTGGTCGTGAGACGGTCAG
AGCGGCGCTTAAGCATGCCGGTTTGCTGTAAAGTTTAG

FIGURE 3D

SYNTHETIC OLIGONUCLEOTIDE FOR dapA
CONSTRUCTION

```
  TTC ACG GGA AGT ATT GTC G
G TAC AAG TGC CCT TCA TAA CAG C
```

FIGURE 3E

OCTOPINE SYNTHASE TERMINATOR SEQUENCE cagctgcttttaatgagatatgcgagacgcctatgatcgcatgatatttgct
ttcaattctgttgtgcacgttgtaaaaaacctgagcatgtgtagctcagat
ccttaccgccggtttcggttcattctaatgaatatatcacccgttactatc
gtattttatgaataatattctccgttcaatttactgattg..........
...........

FIGURE 11A lysC SEQUENCE

```
ATGTCTGAAATTGTTGTCTCCAAATTTGGCGGTACCAGCGTAGCCGATTTTG
ACGCCATGAACCGCAGCGCTGATATTGTGCTTTCTGATGCCAACGTGCGTTT
AGTTGTCCTCTCGGCTTCTGCTGGTATCACTAATCTGCTGGTCGCTTTAGCT
GAAGGACTGGAACCTTGCGAGCGATTCGAAAAACTCGACGCTATCCGCAACA
TCCAGTTTGCCATTCTGGAACGTCTGCGTTACCCGAACGTTATCCGTGAAGA
GATTGAACGTCTGCTGGAGAACATTACTGTTCTGGCAGAAGCGGCGGCGCTG
GCAACGTCTCCGGCGCTGACAGATGAGCTGGTCAGCCACGGCGAGCTGATGT
CGACCCTGCTGTTTGTTGAGATCCTGCGCGAACGCGATGTTCAGGCACAGTG
GTTTGATGTGCGTAAAGTGATGCGTACCAACGACCGATTTGGTCGTGCAGAG
CCAGATATAGCCGCGCTGGCGGAACTGGCCGCGCTGCAGCTGCTCCCACGTC
TCAATGAAGGCTTAGTGATCACCCAGGGATTTATCGGTAGCGAAAATAAAGG
TCGTACAACGACGCTTGGCCGTGGAGGCAGCGATTATACGGCAGCCTTGCTG
GCGGAGGCTTTACACGCATCTCGTGTTGATATCTGGACCGACGTCCCGGGCA
TCTACACCACCGATCCACGCGTAGTTTCCGCAGCAAAACGCATTGATGAAAT
CGCGTTTGCCGAAGCGGCAGAGATGGCAACTTTTGGTGCAAAAGTACTGCAT
CCGGCAACGTTGCTACCCGCAGTACGCAGCGATATCCCGGTCTTTGTCGGCT
CCAGCAAAGACCCACGCGCAGGTGGTACGCTGGTGTGCAATAAAACTGAAAA
TCCGCCGCTGTTCCGCGCTCTGGCGCTTCGTCGCAATCAGACTCTGCTCACT
TTGCACAGCCTGAATATGCTGCATTCTCGCGGTTTCCTCGCGGAAGTTTTCG
GCATCCTCGCGCGGCATAATATTTCGGTAGACTTAATCACCACGTCAGAAGT
GAGCGTGGCATTAACCCTTGATACCACCGGTTCAACCTCCACTGGCGATACG
TTGCTGACACAATCTCTGCTGATGGAGCTTTCCGCACTGTGTCGGGTGGAGG
TGGAAGAAGGTCTGGCGCTGGTCGCGTTGATTGGCAATGACCTGTCAAAAGC
GTGCGCCGTTGGCAAAGAGGTATTCGGCGTACTGGAACCGTTCAACATTCGC
ATGATTTGTTATGGCGCATCCAGCCATAACCTGTGCTTCCTGGTGCCCGGCG
AAGATGCCGAGCAGGTGGTGCAAAAACTGCATAGTAATTTGTTTGAGTAA
```

FIGURE 11B

SYNTHETIC OLIGONUCLEOTIDE FOR *lysC* CONSTRUCTION

```
  TCT GAA ATT GTT GTC TCC AAA TTT GGC GGT AC
G TAC AGA CTT TAA CAA CAG AGG TTT AAA CCG C
```

TRANSGENIC PLANTS OVERPRODUCING THREONINE AND LYSINE

FIELD OF THE INVENTION

The present invention relates to a chimeric gene comprising a DNA sequence coding for an enzyme having aspartate kinase activity and DNA sequences enabling expression of the enzyme in plant cells and subsequent production of high levels of threonine. Transgenic plants containing said gene in their cells produce high levels of threonine and are resistant to phytotoxic amounts of lysine and threonine. Transgenic plants co-transformed with a chimeric gene comprising a DNA sequence encoding an enzyme having aspartate kinase activity and a chimeric gene comprising a DNA sequence encoding an enzyme having dihydrodipicolinate synthase activity, produce high levels of both threonine and lysine and are resistant to phytotoxic amounts of threonine and lysine.

BACKGROUND OF THE INVENTION

The diet of humans and livestock is based largely on plant material. However, crop plants are generally rendered as low nutritional quality food sources because they contain low proportions of several amino acids which are essential for, but cannot be synthesized by, monogastric animals. Therefore synthetic essential amino acids are usually supplied as supplements to grain-based and other diets, in order to increase their nutritional value.

Two of the essential amino acids needed for animal nutrition often missing from crop plants are threonine and lysine. Various attempts have been made in the past to increase the levels of free threonine and lysine in plant tissues by breeding and by mutant selection. In addition, there were attempts to change the composition of the storage proteins accumulated in crop plants, but with minimal success. Either the expression of transgenic storage protein was too low or there were unacceptable quality changes in the product.

Biosynthesis of Aspartate-Family Amino Acids

The essential amino acids lysine, threonine and methionine are synthesized from aspartate by a complex pathway which is similar between bacteria and higher plants.

The biosynthesis of the aspartate-family comprising the amino acids lysine, threonine, methionine and isoleucine is depicted in the diagram of FIG. 1. (Only the major key enzymes and their products are indicated. Curved arrows represent feedback inhibition of activity by the end-product amino acids. AK-aspartate kinase; DHPS-dihydrodipicolinate synthase; HSD-homoserine dehydrogenase; and THD-threonine dehydratase). The aspartate family pathway has been characterized in detail in E. coli by isolation of the specific enzymes involved in the pathway, and later, similar enzymes have been identified and purified from higher plants, showing that the biosynthesis of the aspartate-family amino acids is strikingly similar for E. coli and higher plants (Bryan, J. K. (1980), The Biochemistry of Plants (ed. by B. J. Miflin,) Vol 5: 403–452, Academic Press, N.Y; Umbarger, H. E. (1978) Ann. Rev. Biochem. 47: 533–606).

This biosynthetic pathway involves many enzymes, some of which are common for several or all of the aspartate-family amino acids, while others are specific for individual amino acids. The rate of synthesis of the aspartate-family amino acids is regulated in a complex process of inhibition of the activity of some key enzymes in the pathway, by the relevant amino acid end product. These inhibition processes occur probably through direct interactions between the enzymes and the amino acids, since the amino acids can also inhibit the activity of purified enzyme preparations. The activity of aspartate kinase, the first enzyme in this pathway that is common to all of the aspartate-family amino acids, is feedback inhibited both by lysine and threonine. In addition, lysine also inhibits the activity of the enzyme dihydrodipicolinate synthase, the first enzyme after the branch point that leads to its own synthesis. Similarly, threonine also inhibits the activity of the enzyme homoserine dehydrogenase, and isoleucine inhibits the activity of threonine dehydratase, the first enzyme involved in its own biosynthesis from threonine.

The enzyme aspartate kinase (AK) converts aspartate into 3-aspartyl phosphate, the first of two reactions that are common to all aspartate-family amino acids and lead to the formation of 3-aspartate semialdehyde, an intermediate branch point from which the biosynthesis of lysine proceeds specifically (FIG. 1). Both in E. coli and in plants, several different AK isoenzymes have been identified. AK-III, the product of the E. coli lysC locus utilized in the present invention, appears to be a homodimer containing two identical subunits (Cassan, M. et al. (1986) J. Biol. Chem. 261: 1052–1057; Richaud, C. et al. (1973) Eur. J. Biochem. 40: 619–629). The genetic information of the lysC locus is therefore sufficient to encode an active AK-III isoenzyme. The E. coli lysC gene has been cloned and sequenced (Cassan, M. (1986), see above).

The enzyme dihydrodipicolinate synthase (DHPS) catalyzes the condensation of 3-aspartate semialdehyde with pyruvate to form 2,3-dihydrodipicolinate (FIG. 1). In E. coli, this enzyme is encoded by the dapA locus and appears to be a homotetramer consisting of four identical subunits (Shedlarski, J. G. and Gilvarg, C. (1970) J. Biol. Chem. 245: 1362–1373). The E. coli dapA gene has been cloned and sequenced (Richaud, F. et al. (1986) J. Bacteriol. 166:: 297–300). DHPS activity has also been demonstrated in extracts of many plants and, as with the E. coli enzyme, plant DHPS appears as a single enzyme. All plant DHPSs purified so far were shown to possess activity that is strongly inhibited by lysine alone. In contrast to higher plants, DHPS of E. coli plays only a minor role in the regulation of lysine biosynthesis, apparently because of its lower sensitivity to lysine inhibition (Dauce-Le Reverend, B. et al. (1982) Eur. J. Appl. Microbiol. Biotechnol. 15: 227–231). Indeed, whereas the $I_{50}$ of plant DHPSs range between 10–50 μM lysine, the $I_{50}$ of E. coli DHPS is about 1 mM (Yugari, Y. and Gilvarg, C. (1962) Biochem. Biophys. Acta 62: 612–614).

European Patent Application No. EP 435132 describes a process for the production of amino acid, especially L-lysine (I), which comprises growing a microorganism of the genera Corynebacterium or Brevibacterium which contains recombinant DNA consisting of vector DNA and a sequence for production of proteins with dapA (dihydrodipicolinate synthase) activity, in a nutrient medium, and then recovery of amino acid, the DNA additionally containing a sequence encoding protein with lysC (deregulated aspartate kinase) activity.

The thus transformed bacteria have improved lysine secretion rates.

European Patent Application No. EP 429458 discloses a method of increasing the level of free-L-lysine in a plant comprising (a) introducing a foreign gene into the cells of a plant tissue source and (b) expressing the foreign gene in the cells, where a first DNA sequence of the gene encodes dihydropicolinic acid synthase (DHDPS) which is resistant to feedback inhibition by endogenously-produced free L-lysine. The foreign gene may comprise a second DNA sequence attached to the 5' terminus of the first DNA sequence and which encodes a chloroplast transit peptide (CTP) which localises the DHDPS in the chloroplasts of the cells. The plants are said to produce elevated levels of free lysine.

However, the transformation of plant cells with a gene coding for AK alone or co-transformation with genes coding for AK and DHPS and leading to an increased production of threonine or of threonine plus lysine, respectively, has heretofore not been described.

SUMMARY OF THE INVENTION

The present invention is directed to a chimeric gene construct capable of expression in plant cells with subsequent increased production of threonine, comprising: (a) a DNA sequence coding for an enzyme having AK activity, and (b) DNA sequences enabling expression of the enzyme in plant cells and subsequent production of high levels of threonine.

The invention also relates to an expression vector comprising the chimeric gene construct of the invention.

In another embodiment, the invention provides transgenic plant cells containing a chimeric gene according to the invention or transformed by an expression vector according to the invention, as well as transgenic plants producing high levels of threonine regenerated from said plant cells, and tissues derived from said transgenic plants.

The invention further provides transgenic plants containing in their cells a first chimeric gene comprising a DNA sequence coding for an enzyme having AK activity and a second chimeric gene comprising a DNA sequence coding for an enzyme having DHPS activity, both chimeric genes further comprising DNA sequences enabling expression of the enzymes in the plant cells and subsequent production of high levels of both threonine and lysine.

In a further embodiment, the invention relates to the use of mixtures of lysine and threonine or of analogs or derivatives thereof or of a selective inhibitor of DHPS or AK as selective herbicides in locus where transgenic plants according to the invention are cultivated.

BRIEF DESCRIPTION OF THE DRAWINGS

FIGS. 3a, 3b, 3c, 3d and 3e illustrates the DNA sequences used in the construction of the chimeric gene of FIG. 2: a.—omega sequence; b.—pea rbcS transit peptide sequence; c.—*E. coli* dapA coding sequence for DHPS; d.—synthetic oligonucleotide; e.—octopine synthase (OCS) terminator sequence. Coding DNA sequences are in capital letters; non-coding DNA sequences are in small letters.

FIGS. 11a and 11b illustrate the DNA sequences of the *E. coli* lysC gene coding for AK (a) and of the synthetic oligonucleotide used in the lysC gene construction (b).

DESCRIPTION OF PREFERRED EMBODIMENTS

Figure 1:
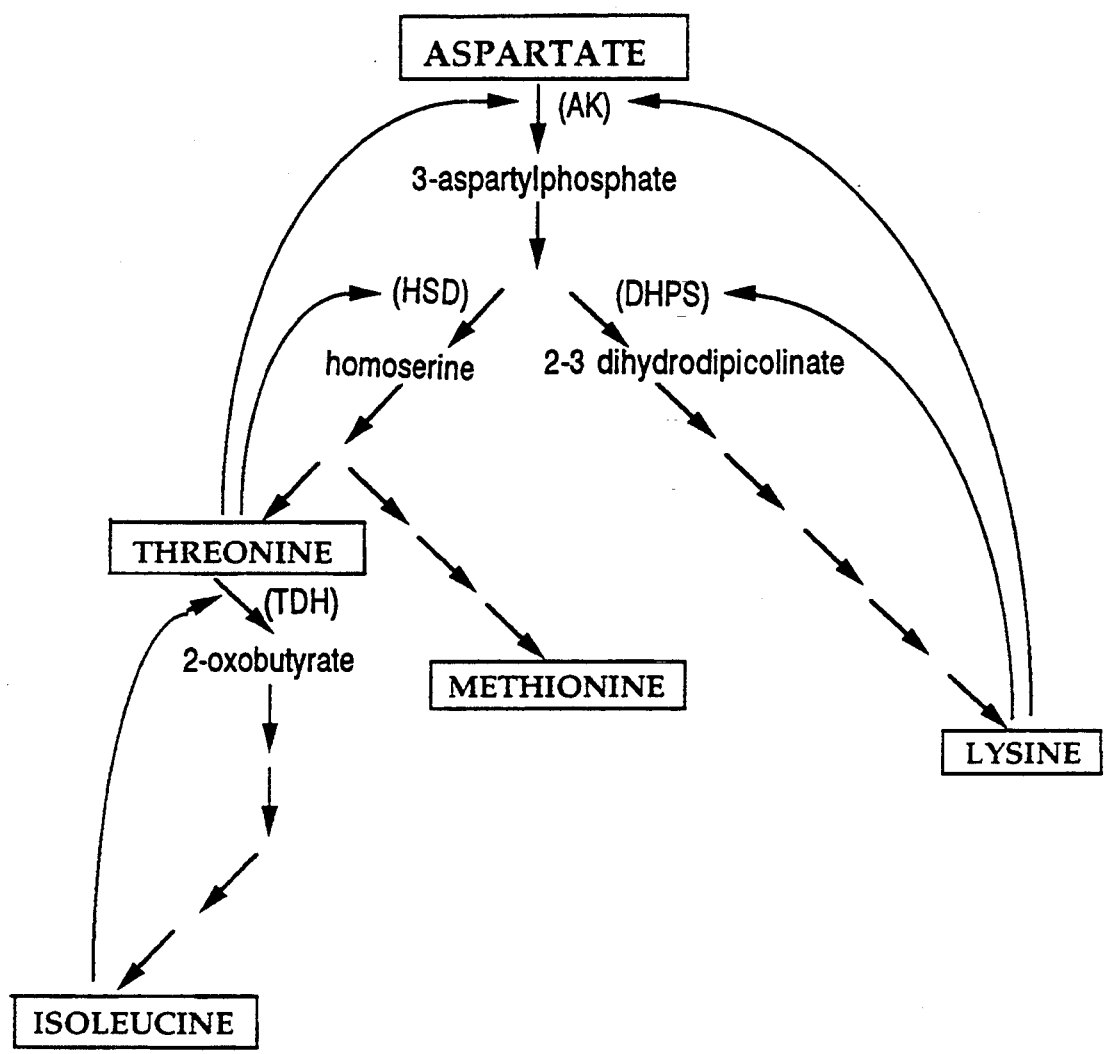
FIG. 1 depicts a diagram of the aspartate-family biosynthetic pathway.

One of the objects of the invention is to generate threonine overproducing plants by transformation of plant cells with a chimeric gene construct comprising: (a) a DNA sequence coding for an enzyme having AK activity, and (b) DNA sequences enabling expression of the enzyme in plant cells and subsequent production of high levels of threonine.

In another embodiment, the invention is directed to threonine plus lysine overproducing plants which contain in their cells both a chimeric gene encoding an enzyme having AK activity and a further chimeric gene encoding an enzyme having DHPS activity, both chimeric genes comprising DNA sequences enabling expression of the enzymes in plant cells and subsequent production of high levels of threonine and lysine.

The DNA sequence coding for an enzyme having AK or DHPS activity may be derived from any suitable source, e.g., from different plant cells or from bacteria, or may be a synthetic gene. In a preferred embodiment, it is derived from exogenous sources that are less sensitive to inhibition by lysine plus threonine than the endogenous plant AK or DHPS enzyme. The preferable exogenous sources are bacteria e.g. *E. coli*, and the most preferred DNA sequence encoding AK activity is the DNA sequence of *E. coli* mutant lysC gene coding for the isoenzyme AK-III, which is less sensitive to lysine than the plant enzyme.

The preferred DNA sequence coding for a DHPS enzyme used according to the invention is the dapA gene from *E. coli* which has a DNA sequence coding for a DHPS enzyme (FIG. 3c), which is less sensitive to lysine inhibition than the plant DHPS enzyme ($I_{1.05}=1000$ μM and 10–50 μM, respectively). The cloning of the dapA gene and its nucleotide sequence were described by F. Richaud, et al. (1986) J. Bacteriol 166: 297–300, whose contents are hereby incorporated by reference in their entirety.

The DNA sequences enabling expression of the enzymes DHPS and AK in plant cells include plant promoters of different kinds, derived from both mono- and dicotiledoneous plants, both non-tissue specific and tissue specific promoters. The preferred promoter is the cauliflower mosaic virus (CaMV) 35S promoter, which is commercially available, and is generally expressed in most, if not all, plant tissues (Guilley, H. et al. (1982) Cell 30: 763–773; Odell, J. T. et al. (1985) Nature 313: 810–812). Other promoters that can be used are inducible promoters, like the light inducible promoter derived from the pea rbcS gene (Coruzzi, G. et al. (1984) EMBO J. 3: 1671–1679) and actin promoter from rice (McElroy, D. et al. (1990), The Plant Cell 2:163–171). Tissue specific promoters are used to direct threonine and lysine overproduction in tissues consumed for food, such as seeds in cereals and tubers in potatoes. Seed-specific promoters, such as phaseoline promoter from beans, shown to be expressed in a seed specific manner in transgenic tobacco plants (Sengupta-Gopalan, C. (1985) Proc. Natl. Acad. Sci. USA 82: 3320–3324) may be used. For the expression in potato tubers, a promoter derived from the potato patatin gone may be used.

The promoter is to be found in the 5' region of the chimeric gene. At the 3' end of the promoter, a short DNA sequence for 5' mRNA non-translated sequence may be added, which enhances translation of the mRNA transcribed from the chimeric gone. An example is the omega sequence derived from the coat protein gene of the tobacco mosaic virus (Gallie, D. R. et al. (1987) Nucl. Acid. Res. 15: 3257-3273) and shown to enhance the translation of mRNAs by 5 to 10 fold.

Since the organelle in which lysine and most of the threonine biosynthesis takes place in higher plants is the chloroplast, the chimeric gene comprises also a DNA sequence coding for a transit peptide, whose role is to translocate the foreign protein from the cytoplasm into the chloroplast (Van den Broeck, G. et al. (1985) Nature 313: 358-363; Schreier, P. H. et al. (1985) EMBO J. 4: 25-32). Thus, according to the invention, a chimeric gene construct comprising a DNA sequence coding for DHPS or AK and a DNA sequence coding for a chloroplast transit peptide will on expression produce a fused DHPS/transit peptide or AK/transit peptide chimeric protein in the cytoplasm of the plant cell, which will then be directed into the chloroplasts, where increased production of the amino acid, lysine or threonine respectively, is thereby obtained.

DNA sequences coding for any kind of chloroplast transit peptide can be used according to the invention, such as DNA sequences derived from the ferredoxin gene that direct proteins into the stroma of the chloroplasts (Smeekens, S. et al. (1985) Nucleic Acids Res. 13: 3179-3193) and DNA sequences from the plastocyanin gene, that direct proteins into the luman of the chloroplast (Smeekens, S. et al. (1985), Nature 317: 456–458). The preferred DNA sequence is the one coding for the transit peptide derived from the pea rbcS-3A gene (shown in FIG. 3b and Fluhr, R. et al. (1986) EMBO J. 5: 2063-2071).

Downstream to the DNA sequence coding for the transit peptide, the coding DNA sequence of the enzyme is fused and in the 3' end of the chimeric gene a terminator DNA sequence containing the 3' transcription termination and polyadenylation signal of the mRNA from the chimeric gene is installed. Terminator DNA sequences comprised within the 3' flanking DNA sequences of any cloned genes can be used, e.g., from the pea rbcS gene, the wheat glutenin gene, and the bean phaseoline gene. The preferred terminator is comprised within the 3' flanking DNA sequence derived from the octopine synthase gene of the Ti plasmid of *Agrobacterium tumefaciens* (FIG. 3e and Greve, H. D. et al. (1983) J. Mol. Appl. Genet. 1: 499-511).

Figure 2:
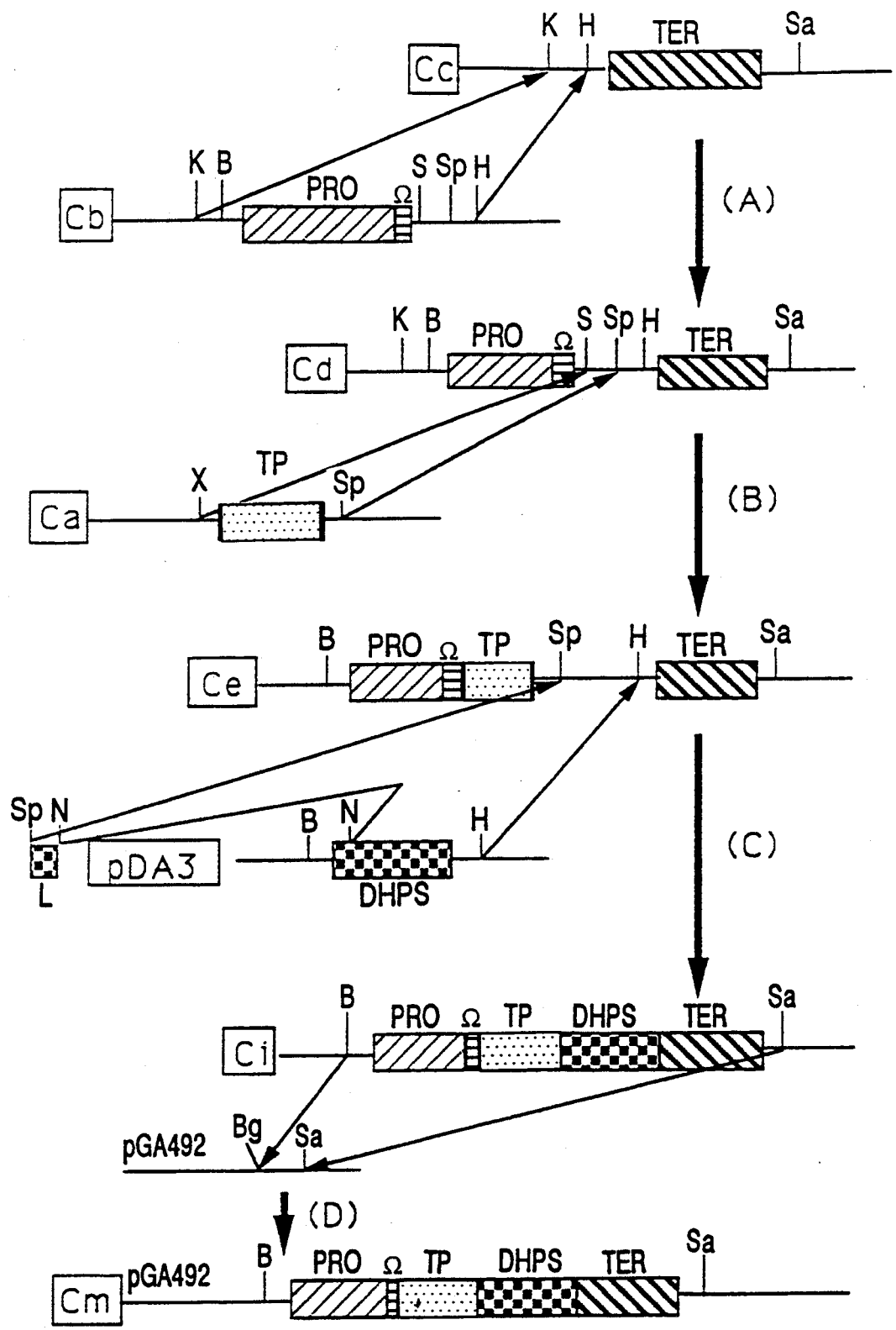
FIG. 2 is a schematic diagram of the chimeric gene for the expression of *E. coli* DHPS and its construction. B=BamI, H=HindIII, K=KpnI, N=NruI, S=SalI, Sa=SacI, Sp=SphI, X=XbaI, PRO=35S promoter, L=synthetic linker, Ω=omega, TER=OCS terminator, TP=rbcs transit peptide.

The chimeric gene construct shown in FIG. 2 comprising the DNA sequence encoding DHPS has the CaMV 35S promoter in the 5' region linked to the 5' end of the omega DNA sequence, the omega DNA sequence is linked to the 5' end of the DNA sequence coding for the chloroplast transit peptide derived from the pea rbcS-3A gene, which is linked to the 5' end of the coding sequence of the *E. coli* dapA gene coding for DHPS, which is linked to the 5' end of the octopine synthase terminator sequence.

Figure 12:
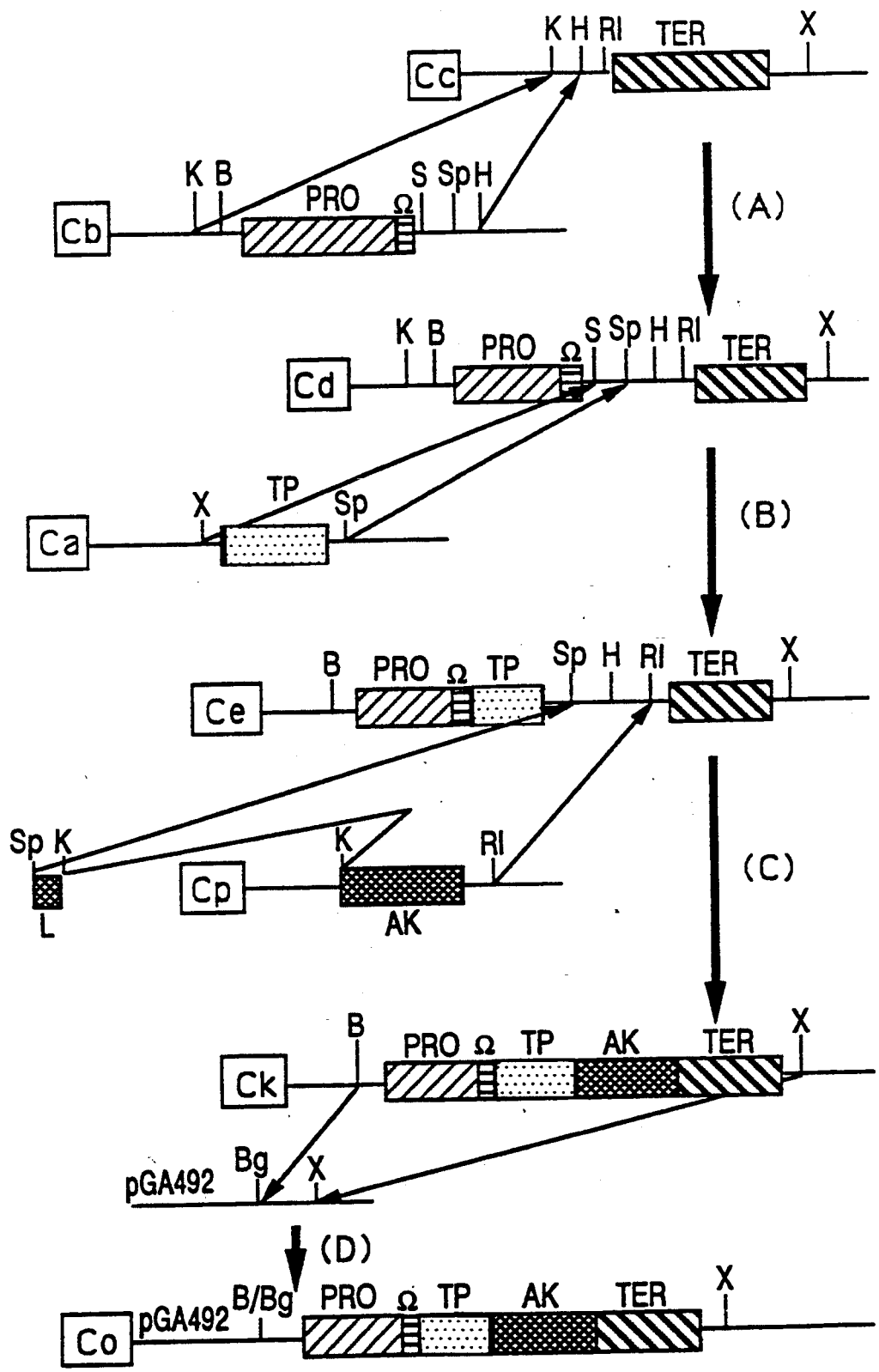
FIG. 12 is a schematic diagram of the chimeric gene for the expression of *E. coli* AK and its construction. B=BamHI, Bg=BglII, H=HindIII, K=KpnI, RI=EcoRI, S=SalI, Sp=SphI, X=XbaI, PRO=35S promoter, L=synthetic linker, Ω=omega, TER=OCS terminator, TP=rbcs transit peptide.

The chimeric gene construct shown in FIG. 12 has a similar structure, but for the coding sequence of the mutant *E. coli* lysC allele coding for a desensitized AK-III instead of the *E. coli* dapA gene.

The chimeric gene constructs can be subcloned into expression vectors, such as the Ti plasmids of *Agrobacterium tumefaciens*, the preferred plasmid being the pGA492 binary Ti plasmid of *Agrobacterium tumefaciens* (An. G. (1986) Plant Physiol. 81: 86-91).

The expression vector comprising the chimeric gene is then introduced into plant cells. Any kind of transformation protocol capable of transferring DNA to either monocotiledonous or dicotiledonous plant cells can be used. Examples are: transformation by direct DNA transfer into plant cells by electroporation (Dekeyser, R. A. et al, (1990) The Plant Cell 2: 591–602); direct DNA transfer to plant cells by PEG precipitation (Hayashimoto, A. et al. (1990) Plant Physiol. 93: 857-863); direct DNA transfer to plant cells by balistic bombardment (Gordon-Kann, W. J. et al. (1990) The Plant Cell 2: 603–618) and DNA transfer to plant cells via infection with Agrobacterium. The preferred method is via infection of plant cells with *Agrobacterium*

*tumefaciens* using the leaf-disk protocol (Horsch, R. B. et al. (1985) Science 227: 1229–1231).

The methodology used here for tobacco, which can be easily transformed and regenerated in tissue culture and for potato, can be used to improve crop plants like rice, maize, wheat and barley.

Transformed plants are then selected by resistance to kanamycin or other antibiotics like hygromycine. Selection for lysine and/or threonine overproducing genotypes at the cultured cell and intact plant levels may be performed by growth on media containing lysine plus threonine or the lysine analog AEC.

Plants containing in their cells both the chimeric gene comprising the AK encoding sequence and the chimeric gene comprising the DHPS encoding sequence can be obtained by crossing between transgenic plants expressing AK and transgenic plants expressing DHPS. These plants overproduce both threonine and lysine, the production of lysine being higher than the production of the parental transgenic plants expressing DHPS. In an alternative, the plants can be obtained by cotransformation of plant cells with expression vectors comprising the AK and the DHPS encoding sequences and regeneration of the plants from said cells.

In another embodiment, the invention relates to the use of a mixture of lysine and threonine or their derivatives or any other selective inhibitor of plant AK and DHPS as selective herbicides with the transgenic plants of the invention.

In this approach, it is taken into consideration that lysine and threonine do not exert end product inhibition on the bacterial enzymes DHPS and mutant AK, while they inhibit the plant enzymes. Plants lacking the bacterial desensitized aspartate kinase are lethally inhibited by a mixture of lysine and threonine due to end product inhibition on the plant aspartate kinase, while the transgenic plants are more resistant.

Thus, according to the invention, lysine and threonine, their derivatives, or any other selective inhibitor of the plant enzymes AK and DHPS, can be used as selective herbicides allowing excellent weed control, only the transgenic crop plants being resistant. In this way natural herbicides with low mammalian toxicity and high crop selectivity are obtained.

Figure 13:
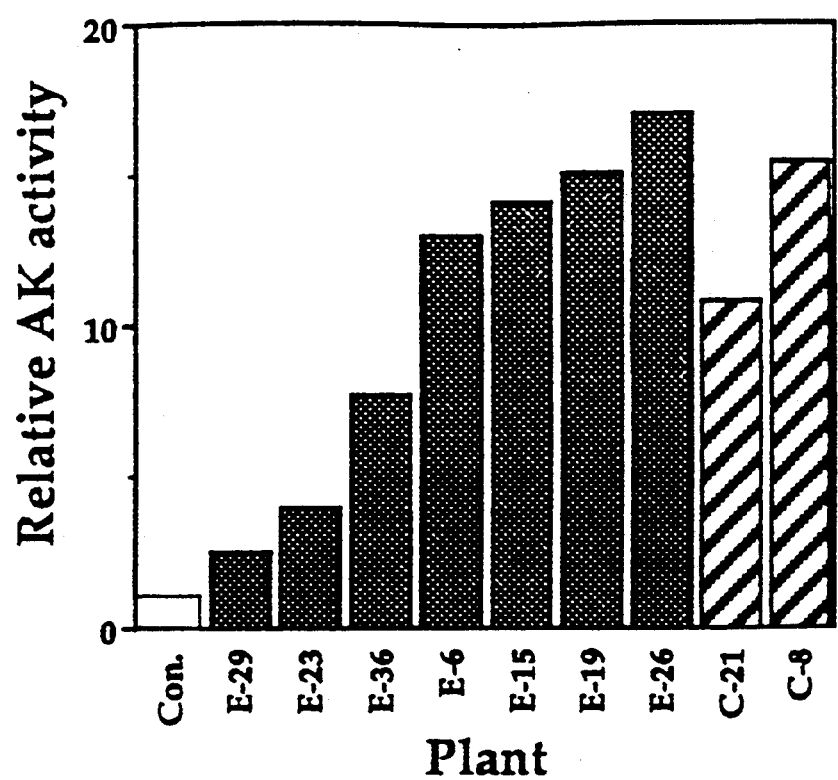
FIG. 13 shows the relative AK activity in the leaves of the transgenic tobacco plants.
Figure 14:
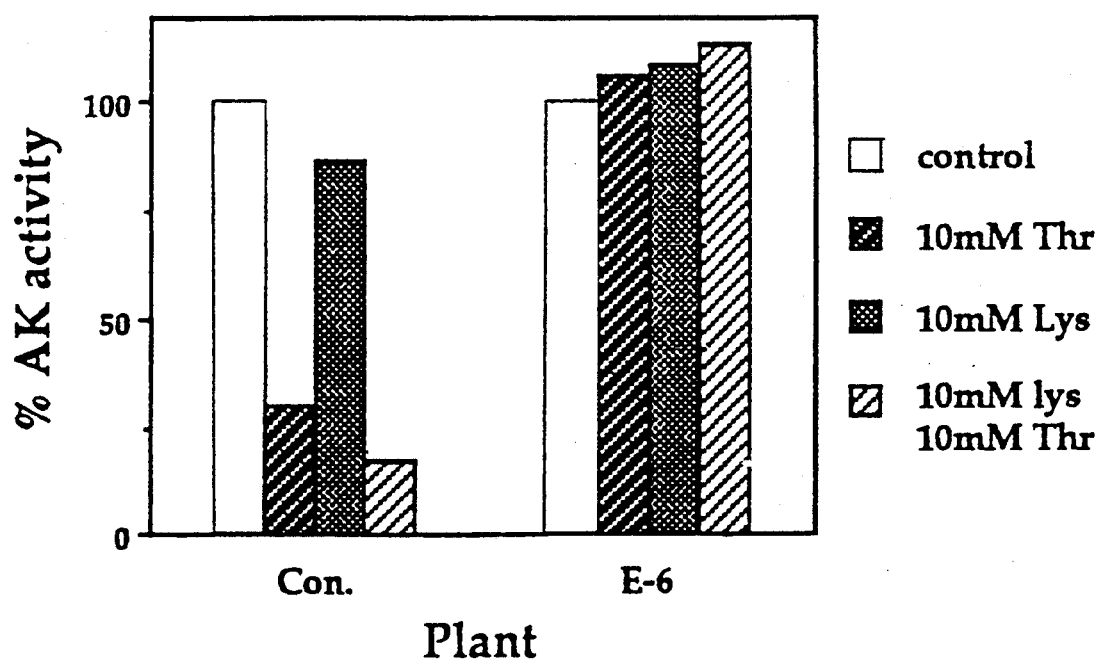
FIG. 14 shows the sensitivity of the AK activity in the leaves of the transgenic tobacco plants to inhibition by lysine and threonine.

Both tobacco and potato plants were transformed with chimeric gene contructs comprising the AK encoding sequence. There was between 2 and 18 fold higher activity of both the chloroplastic and the cytoplasmic enzymes after insertion of the chloroplastic (containing the transit peptide) and cytoplasmic (without transit peptide) constructs into transgenic tobacco plants (FIG. 13). Free threonine levels were increased more than 7 times in both leaves (FIG. 15) and seeds (FIG. 17) of the transgenic tobacco plants with chloroplastic constructs, and about 4 time with cytoplasmic constructs. This can represent about a 50% increase in total threonine in leaves. When wild type aspartate kinase activity was measured in vitro, threonine alone was able to suppress 70% of the activity, and lysine very little. A mixture of the two gave the additive suppression (FIG. 14). The in vitro activity of the mutant bacterial enzyme was completely unaffected by these amino acids, separately and in mixture in the transgenic plants. This inhibition on an enzyme in vitro carried over to the in vivo situation; a mixture of the two amino acids was phytostatic to wild type plants but had little effect on the transgenic plants, allowing the transgenic plants to continue normal growth and development (FIG. 22).

Figure 7:
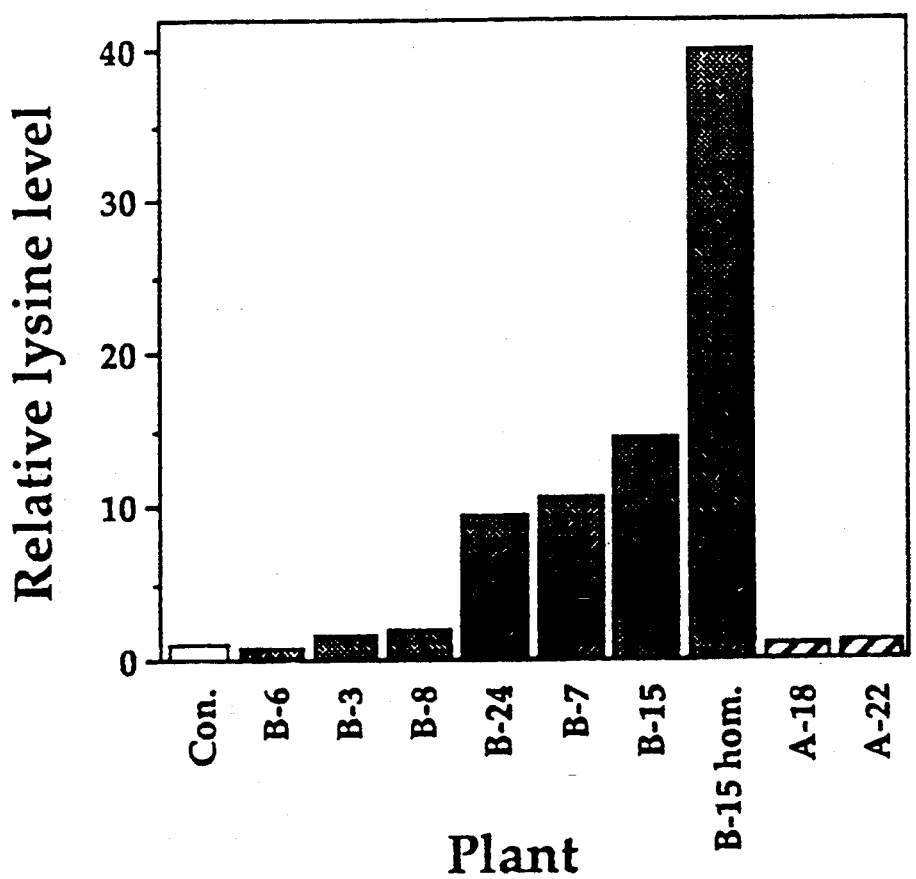
FIG. 7 shows the relative levels of free lysine in leaves of transgenic tobacco plants.
Figure 8A:
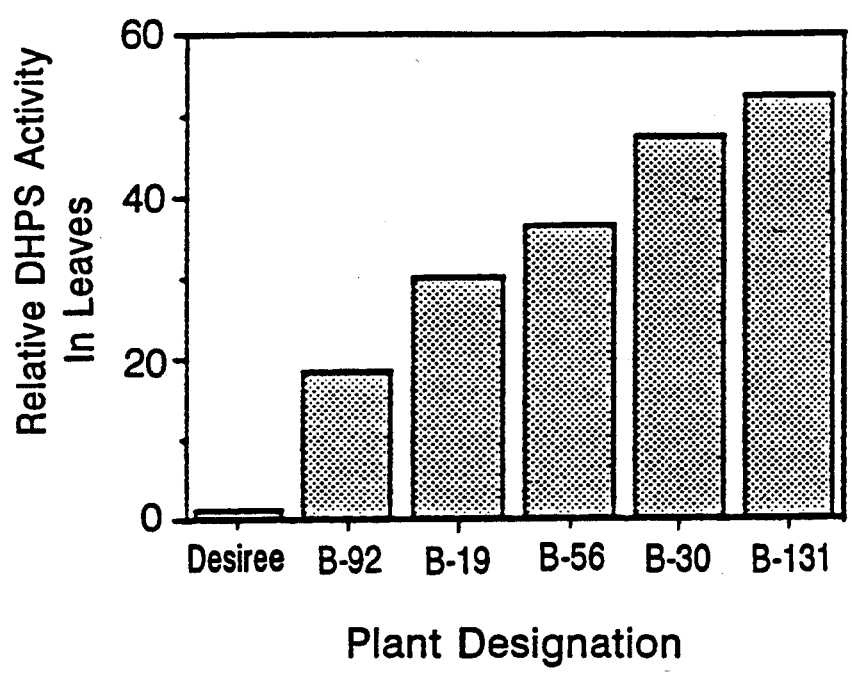
FIG. 8 shows the relative DHPS activity in leaves (A), roots (B) and tubers (C), of transgenic potato plants.
Figure 8B:
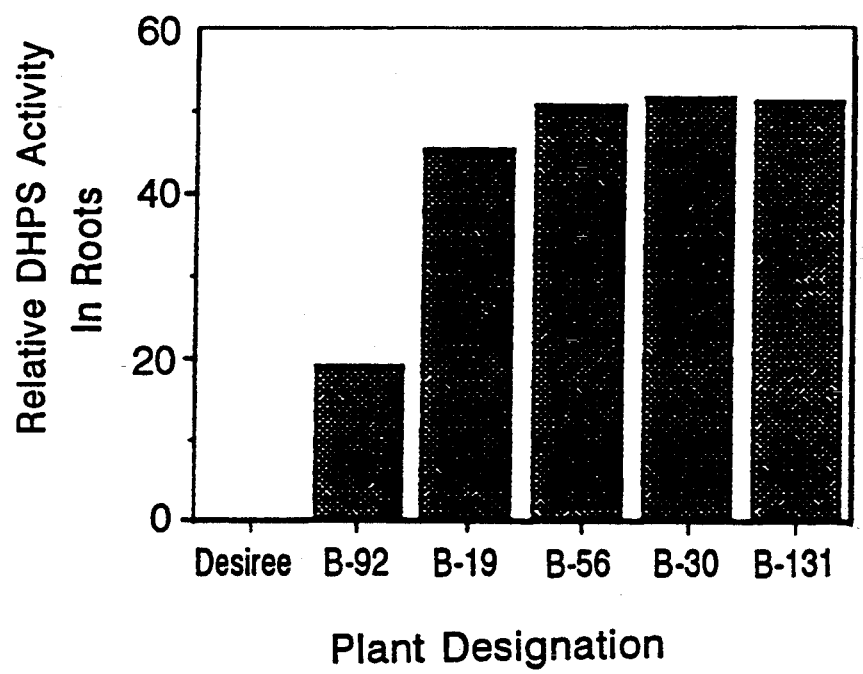
Figure 8C:
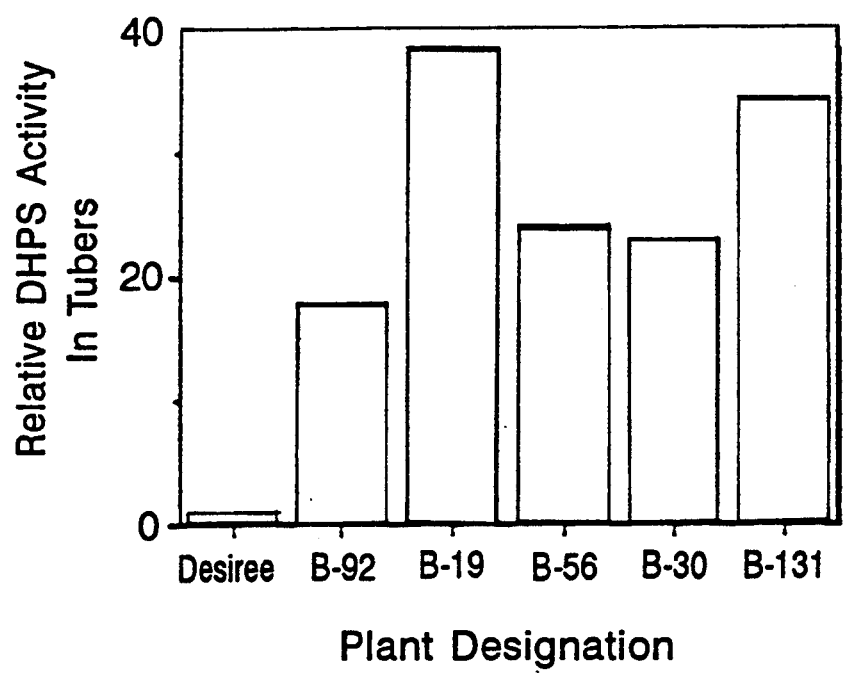

Similar constructs were made with bacterial DHPS genes and plants regenerated. The activity of DHPS increased about 30 fold above wild type in transgenic tobacco leaves (FIG. 4); >50 fold in potato leaves and roots and >35 fold in potato tubers (FIG. 8). This was matched by a >4 fold increase in free lysine in potato leaves and roots, a 3 fold increase in tubers (FIG. 10) and about 40 fold increases in tobacco leaves (FIG. 7). The enzyme in transgenic plants was much more resistant to feedback inhibition by lysine than the enzyme activity from wild type plants, both in potato (FIG. 9) and tobacco (FIG. 5). Thus lysine affects both enzyme activities but the bacterial DHPS is only about 50% inhibited by 1 mM and the plant DHPS inhibited to the same extent by 27 $\mu$M.

Figure 21:
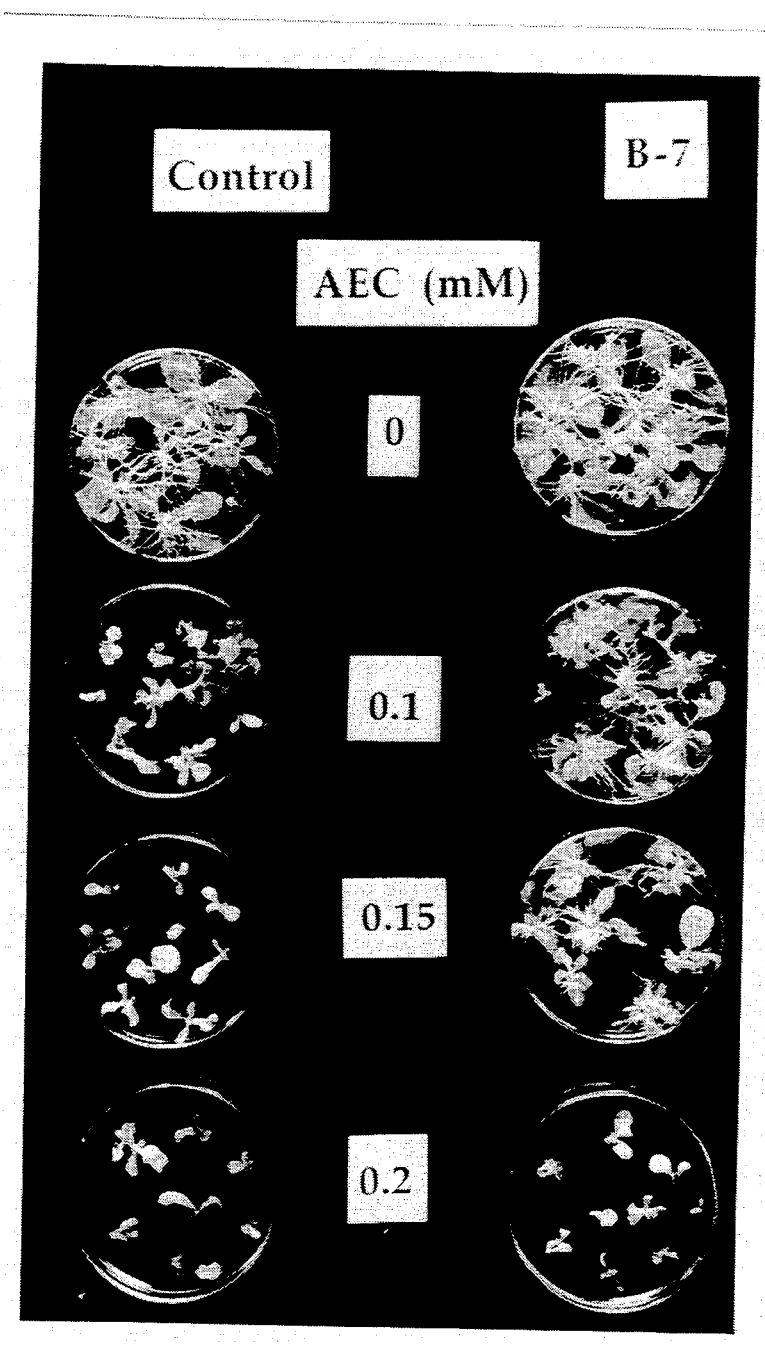
FIG. 21 illustrates the resistance of the transgenic tobacco shoots to aminoethylcysteine (AEC).

Aminoethyl-L-cysteine (AEC) is a lysine analog that is highly phytotoxic due to competition with lysine for incorporation into proteins. The transgenic plants that overproduce lysine due to the insertion of the bacterial DHPS are much less sensitive to AEC (FIG. 21).

Thus, the present invention relates also to a method of rendering a plant resistant to a mixture of lysine and threonine, to their derivatives or to any selective inhibitor of the plant enzymes AK and/or DHPS, which comprises: (a) transforming a plant cell with a chimeric gene comprising a DNA sequence coding for an enzyme having AK activity, and optionally with a further chimeric gene comprising a DNA sequence coding for an enzyme having dihydrodipicolinate synthase (DHPS) activity, both chimeric genes further comprising a plant promoter, a plant polyadenylation and termination sequence, and a DNA sequence coding a chloroplast transit peptide fused to the 5'-end of the DHPS encoding sequence and optionally fused to the 5'-end of the AK encoding sequence; (b) selecting a transformed cell whose growth is resistant to inhibition by a mixture of lysine and threonine, to derivatives thereof or to any selective inhibitor of plant AK and/or DHPS; and (c) regenerating a resistant plant from said plant cells.

The invention also relates to a method of controlling the growth of weeds at a locus where transgenic plants according to the invention are being cultivated which comprises applying to said locus an effective amount of a derivative of lysine or threonine, or of a selective inhibitor of the plant enzymes AK and/or DHPS, or of a mixture of lysine and threonine.

Derivatives of lysine and threonine that can be used according to the invention include, but are not limited to, salts, esters, amides, and other substituted lysine and threonine derivatives and analogs. Inhibitors of AK and DHPS include lysine analogs, such as S-(2-aminoethyl)-L-cysteine (AEC), threo-4-hydroxy-L-lysine (THL), DL-homolysine, $\epsilon$-methyl-L-lysine and DL-allo-$\delta$-hydroxylysine (DHL). They may be used alone or in mixture. Another inhibitor of the plant enzyme AK, S-adenosyl-L-methionine (SAM) may be used together with lysine or AEC.

The invention will now be illustrated by the following non-limitative examples.

EXAMPLES

Example 1

Plasmids for the construction of the chimeric gene for expression of DHPS

The construction of the plasmid pDA3, Ca, Cb and Cc used for the construction of the chimeric gene as depicted in FIG. 2, was carried out as follows:

1.1. Plasmid pDA3

The *E. coli* dapA gene having a coding sequence for DHPS (FIG. 3c) was cloned from a bacteriophage lambda library by complementation of a dapA minus *E. coli* strain (Richaud F. et al. (1986), see above). Plasmid pDA3 was obtained by cloning a 1.1kd BstN1 fragment containing the dapA gene into the HincII site of pUC9 (Pharmacia).

1.2 Plasmid Cb

A 0.4 kb DNA fragment containing the promoter region of the CaMV 35S gene (PRO) (Clontech) was fused at its 3' end to a 68 bp synthetic DNA fragment containing the omega sequence ($\Omega$) of tobacco mosaic virus (TMV). The 35S promoter plus the omega DNA were cloned between the BamHI(B) and SalI(S) sites of pUC18 (Pharmacia) to form plasmid Cb. The DNA sequence of omega is shown in FIG. 3a.

1.3. Plasmid Cc

A 0.7kb fragment (TER) containing the transcription termination and polyadenylation signal of the *Agrobacterium tumefaciens* octopine synthase (OCS) gene was cloned into the SmaI site of Bluescript SK+ plasmid (Stratagene). The BamHI site in the polylinker was then eliminated by BamHI digestion, followed by "fill in" reaction with Klenow and ligation to form the plasmid Cc (FIG. 2).

1.4. Plasmid Ca

The pea rbcS-3A gene contains an SphI site located at the 3' end of the DNA sequence coding for the transit peptide (TP). An XbaI (X) site was also introduced into this gene three nucleotides upstream to the translation start site by site directed mutagenesis (Kunkel, T. A. et al. (1987) Methods in Enzymol. 154: 367–382). The XbaI to SphI DNA fragment coding for the transit peptide was cloned between the XbaI and SphI site of pUC18 to form the plasmid Ca. The pea rbcs-3A transit peptide coding DNA sequence is shown in FIG. 3b.

Example 2

Construction of the chimeric gene for expression of DHPS

The DNA vectors were constructed by standard procedures. Plasmid DNAs were purified by banding in CsCl-ethidium bromide gradients (Maniatis, T. et al, (1982) Molecular Cloning: A Laboratory Manual, Cold Spring Harbor Labor.). DNA restriction fragments were isolated by electrophoretic separation in agarose gels followed by purification with glass beads (using the Geneclean kit of bio 101). Restriction endonucleases (Boehringer, New England Biolabs), T$_4$DNA ligase (Boehringer) and the large fragment of *E. coli* DNA polymerase (New England Biolabs) were used as recommended by the suppliers. *E. coli* transformation was carried out with frozen competent bacteria (Maniatis, et al, (1982), see above) using the *E. coli* strain DH-5$\alpha$ (Clontech).

A schematic diagram of the construction of the chimeric gene is shown in FIG. 2. The subcloning steps A to D were performed in *E. coli*.

In step (A), plasmid Cb was digested with KpnI (K) and HindIII (H)and the 0.5 kb DNA fragment containing the 35S promoter (PRO) and omega ($\Omega$) leader was ligated with a KpnI and HindIII digested Cc plasmid to create plasmid Cd.

In step (B), plasmid Ca was digested with XbaI (X); the XbaI cohesive end was made blunt-ended using the large fragment of DNA polymerase I. Then the plasmid was digested with SphI (Sp) and the 0.18 kb DNA fragment coding for the rbcS-3A transit peptide (TP) was isolated. Plasmid Cd was digested with SalI (S), made blunt ended with DNA polymerase I, digested with SphI and ligated with the 0.18 kb fragment that was isolated from plasmid Ca to form plasmid Ce.

In step (C) plasmid pDA3 was digested with NruI (N) and the HindIII (H) and the 0.9 kb DNA fragment containing the entire coding sequence of the dapA gene except for 22 bp at the 5' end (DHPS), was isolated. In order to restore these 22 bp of DNA a double stranded synthetic oligonucleotide linker (L) was synthesized (sequence shown in FIG. 3d), that contained a NruI (N) site at its 3' end and an SphI (Sp) site at its 5' end. The isolated 0.9 kb DNA fragment and the synthetic oligonucleotide were ligated into the SphI and HindIII sites of plasmid Ce to form plasmid Ci which contained the entire chimeric gene.

In step D, plasmid Ci was digested with SacI (Sa) and BamHI (B) and the 2.38 kb DNA fragment containing the chimeric gene was isolated and ligated into the SacI and BglII sites of plasmid pGA492 to create plasmid Cm.

In order to construct the chimeric gene without the DNA sequence coding for the transit peptide, step B was omitted, so that in step C plasmid Cd was utilized instead of plasmid Ce.

Example 3

Transformation of tobacco plants

The plasmid Cm of Example 2 was immobilized from *E. coli* to *Agrobacterium tumefaciens* by the triparental mating protocol (Ditta, G. et al. (1980) Proc. Natl. Acad. Sci. USA 77: 7347) as follows: *E. coli* harboring the plasmid Cm was mixed with the *Agrobacterium tumefaciens* strain LBA4404 (Stratagene) and with the *E. coli* strain harboring the plasmid pRK 2013 (Stratagene), that contains genes needed for DNA immobilization between bacteria, and were allowed to grow overnight on an antibiotic-free rich medium. *Agrobacterium tumefaciens* LBA4404 containing the plasmid Cm was selected on rich medium containing 100 $\mu$g/ml rifampicin, 5 $\mu$g/ml tetracycline and 25 $\mu$g/ml kanamycin and utilized to infect tobacco leaf disks employing the leaf disk protocol (Horsch, R. B. et al. (1985) Science 227: 1229–1231). Tobacco leaf disks were dipped in an overnight grown culture of *Agrobacterium tumefaciens* harboring the plasmid Cm and then allowed to incubate for two days on MS medium agar plates (Murashige, T. and Skoog, F. (1962) Physiol. Plant. 15: 473–497) containing 2 mg/l kinetin and 0.8 mg/l indoleacetic acid IAA). The disks were then moved to plates containing the above modified MS medium plus 100$\mu$g/ml kanamycin and 500$\mu$/ml carbenicilin and allowed to incubate until shoots were regenerated. Regenerated shoots were transferred to a rooting medium (Nitsch, J. P. (1969) Phytomorphology 19: 389–404) supplemented with 100 $\mu$g/ml kanamycin to allow root formation. The transgenic plants were planted in pots and moved to the greenhouse.

Example 4

Analysis of DHPS activity and content of free lysine in leaves of the transgenic tobacco plants Two types of transgenic plants were utilized. The chloroplastic type contained the chimeric DHPS gene shown in FIG. 2. The cytoplasmic type, that was used for comparison purposes, contained a chimeric DHPS gene lacking the DNA sequence coding for the transit peptide. In the transgenic plants containing the cytoplasmic type chimeric gene, the *E. coli* DHPS was apparently expressed in the cytoplasm.

Transgenic plants were screened for an elevated DHPS activity. DHPS activity was assayed in crude extracts from leaves of transgenic plants by the O-amino-benzaldehyde (O-ABA) assay of Yugari and Gilvarg (Yugari Y. and Gilvarg C., (1965) J. Biol. Chem. 240: 4710–4716) with slight modifications. Leaves from axenic tobacco plants grown in culture were homogenized with a mortar and pestle in an equal volume of cold 100 mM Tris-HCl pH 7.5 containing 1 mM phenylmethylsulfonylfluoride and 0.5 μg/ml leupeptine. Following 5 min centrifugation (16,000 xg, 4° C.) the supernatant was collected and its protein concentration was determined by the method of Bradford.

Figure 4:
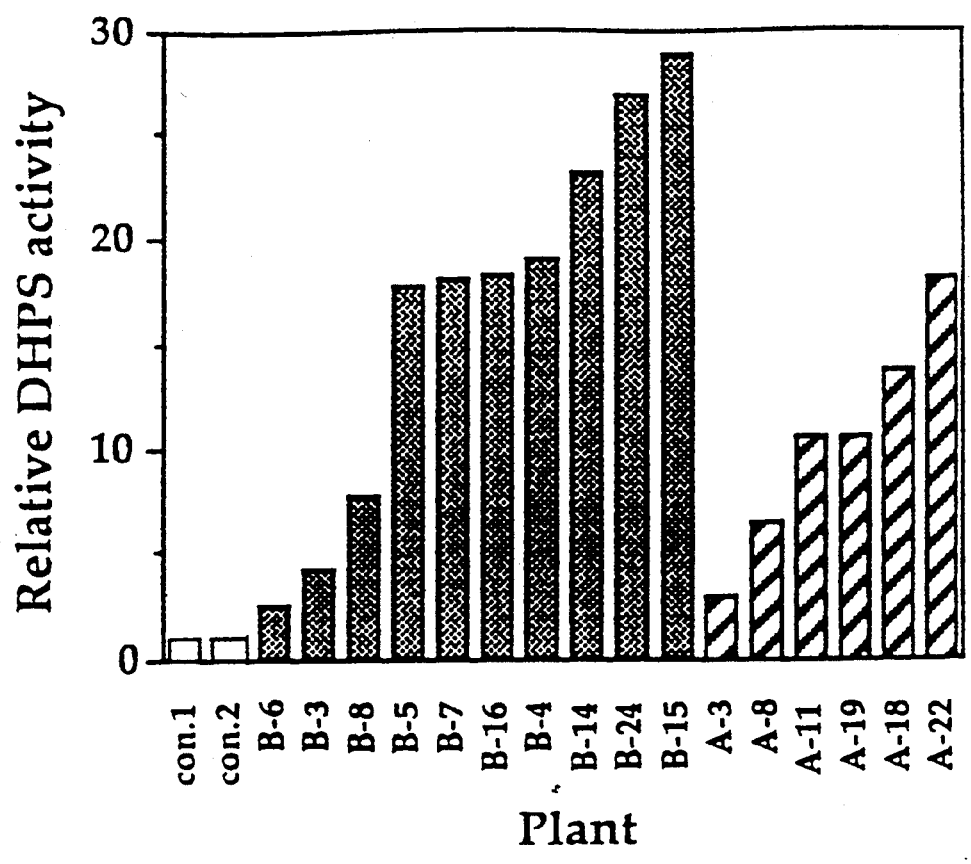
FIG. 4 shows relative DHPS activity in the transgenic tobacco plants.
Figure 5:
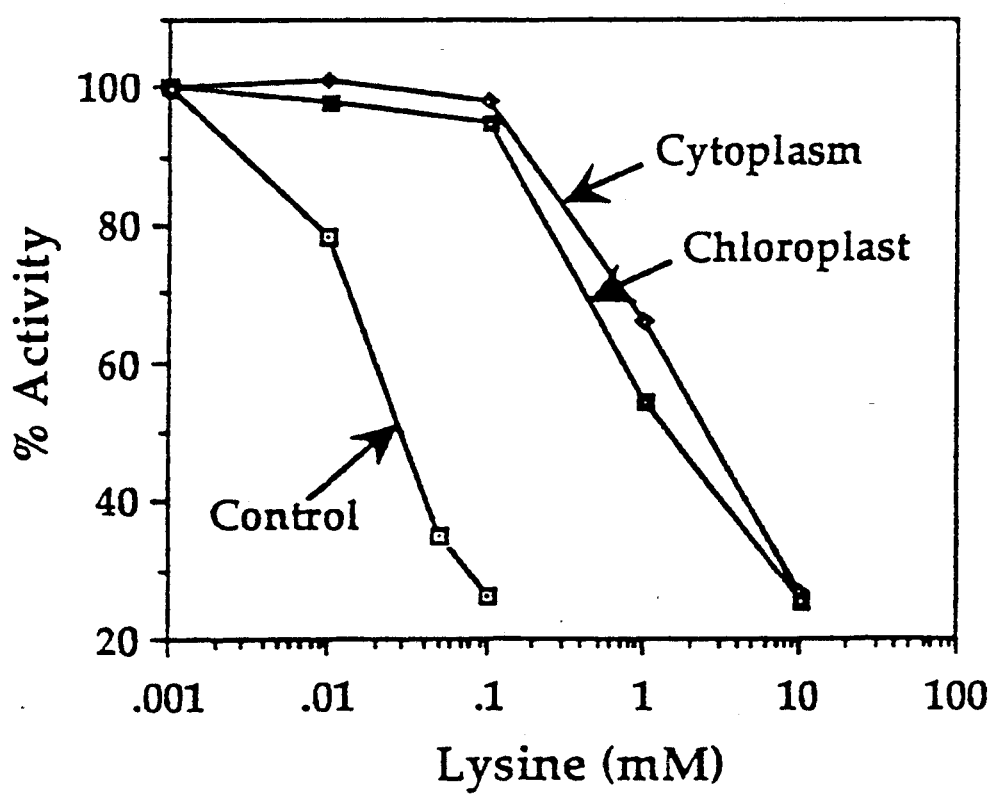
FIG. 5 shows the sensitivity of DHPS activity from the transgenic tobacco plants to inhibition by lysine.

In FIG. 4, DHPS activity assayed in crude extracts from leaves of each transgenic genotype (average of 2 measurements for each transgenic genotype) is plotted relative to the average DHPS activity of two control untransformed plants (Con.), which was given the value of 1. (B-3 to B-15) Transgenic genotypes expressing DHPS in the chloroplast; (A-3 to A-22) Transgenic genotypes expressing DHPS in the cytoplasm. All of the transgenic genotypes possessed higher DHPS activity than the control plants. The transgenic plant B-15 contained the highest DHPS activity which was close to 30 fold higher than that of the control plants.

FIG. 5 shows the sensitivity of DHPS activity from the transgenic tobacco plants to lysine inhibition. DHPS activity was assayed as above but in the presence of increasing lysine concentrations. At each lysine concentration, DHPS activity is presented as a percentage of the activity in extracts with no lysine added (average of two plants for each transformation). (Control)—non-transformed plants; (Cytoplasm)—average DHPS activity of plants A-11 and A-22 containing the cytoplasmic-type *E. coli* DHPS; (Chloroplast)—average DHPS activity of plants B-7 and B-15 containing the chloroplastic-type *E. coli* DHPS. The elevated levels of DHPS activity in the transgenic plants clearly resulted from the expression of the *E. coli* enzyme in them. DHPS activity in the transgenic plants was less sensitive to lysine inhibition than DHPS activity in the control plants, as shown in FIG. 5. The $I_{50}$ for DHPS inhibition by lysine in the transgenic plants was measured to be 1.6 mM, similar to the inhibition of DHPS activity by lysine in *E. coli* cells. In contrast, the $I_{50}$ for DHPS inhibition by lysine in the control nontransformed plants was 27 μM.

Figure 6:
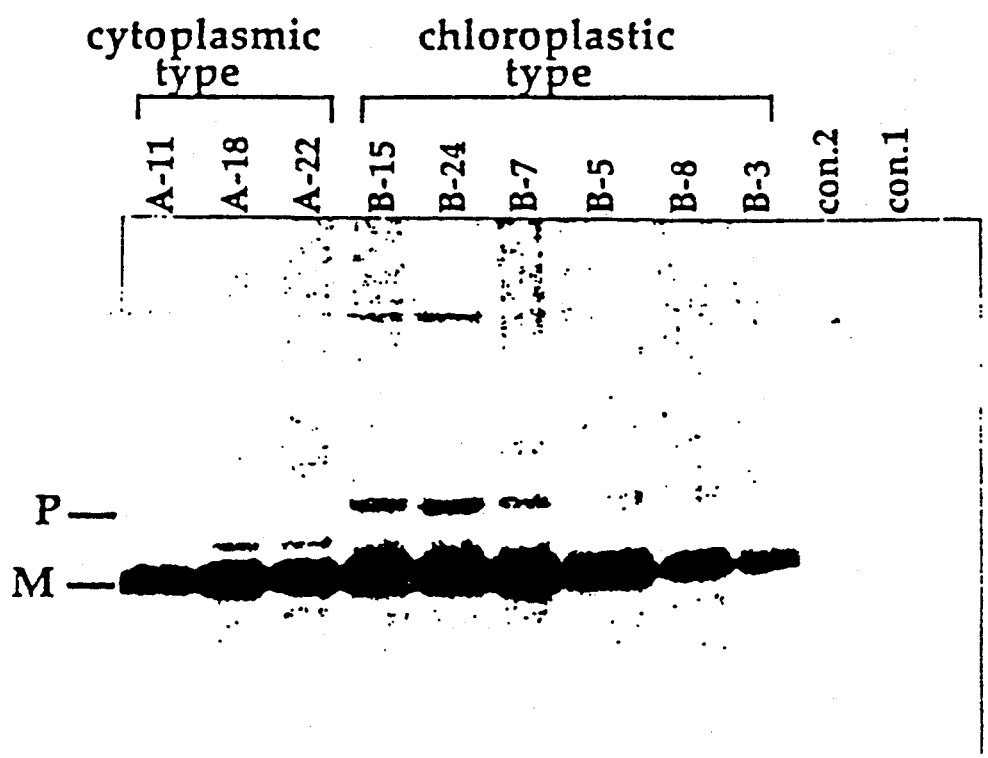
FIG. 6 is a Western blot of the *E. coli* DHPS of the cytoplasmic and chloroplastic types in tobacco transgenic plants.

FIG. 6 shows Western blot analysis of the *E. coli* DHPS in transgenic plants. Leaves were homogenized and the supernatants collected. Protein (120 μg) was fractionated by SDS-PAGE. Western blot was performed according to Burnette (Anal. Biochem. 112: 195–203 (1981)). Proteins extracted from leaves of control and transgenic plants containing the cytoplasmic- and chloroplastic-type enzymes were reacted in Western blots against antibodies specific to *E. coli* DHPS. (M) Band corresponding in MW to the natural *E. coli* DHPS. (P) Band corresponding to the expected size of the precursor *E. coli* DHPS containing the chloroplast transit peptide.

The content of free lysine in leaves of the transgenic plants was then measured and plotted relative to the average level of free lysine in 14 control nontransformed plants (Con.). Leaves (100 mg fresh weight) were harvested from each plant, free amino acids were extracted immediately and their concentration was determined with the O-phthaldehyde reagent followed by measuring the 335/447 nm fluorescence. Amino acid composition was determined by loading a sample of 11 nmoles on an amino acid analyzer. The level of lysine in each sample was normalized to the level of free lysine in control plants. The results are shown in FIG. 7. The average lysine level in the control plants was 130 nmol/g fresh weight (FW). (B-3 to B-24; B-15 hom is a homozygous B-15 plant) Transgenic plants expressing the chloroplastic-type DHPS; (A-18 and A-22) Transgenic plants expressing the cytoplasmic-type DHPS.

Example 5

Potato Transformation 5.1 Transformation of potato plants

Tubers of S. tuberosum cv. "Desiree" were surface-sterilized in 1% sodium hypochlorite for 20 min, then washed 3 times in sterile distilled water, and transformed by the procedure of Sheermann and Bevan (Sheermann S. and Bevan, M. W. (1988) Plant Cell Rep. 7: 13–16) with some modifications. Three mm thick tuber discs were incubated for 20 min in overnight grown cultures of *Agrobacterium tumefaciens* harboring the plasmid Cm. After blotting on sterile paper the discs were cultured in solidified (1% agar) MS medium (Murashige, T. and Skoog, F., (1962) Physiol. Plant. 15: 473–497) supplemented with 2 mg/liter zeatin riboside and 1 mg/liter indole-3-aspartic acid. After 48 h of co-cultivation the discs were transferred to the same medium but with the addition of 500 μg/ml carbenicillin and 100 μg/ml kanamycin. After about one month of culture (24° C., 40 μE m$^{-2}$ s$^{-1}$ light fluence), shoots were regenerated. These were further rooted on solidified (0.8% agar) Nitsch medium supplemented with 100 μg/ml kanamycin, 1 mg/liter indole-3-butyric acid (IBA) and 250 μg/ml carbenicillin. Regenerated shoots that rooted in the presence of kanamycin were transferred to the greenhouse for further observation, propagation and analyses.

5.2. Establishment of root cultures

In order to establish potato root cultures, root sections (1–2 cm) were cultured in 9 cm Petri dishes containing 6 ml of liquid MS medium supplemented with 2 mg/liter indole-3-butyric acid. Cultures were kept at 25° C. on a gyratory shaker (100 rpm) for 10 days.

5.3 In vitro tuber formation

In order to induce in vitro tuberization, shoot-sections (about 4–5 cm long) were placed horizontally in vessels containing 20 ml of liquid tuber inductive medium, consisting of half strength MS salts supplemented with 8% (w/v) sucrose, 5 mg/liter kinetin and 5 mg/liter ancymidol (α-cyclopropyl-4-methoxy-α-pyrimidin-5-yl-benzyl alcohol). After 10 days on a gyratory shaker (100 rpm), at 22° C. under 16 h light regimes providing 20 μE m$^{-2}$s$^{-1}$, minitubers (0.5 cm in diameter) were harvested, their fresh weight was determined and analyzed for DHPS activity and lysine content.

Example 6

Analysis of DHPS activity and content of free lysine in transgenic potato plants Analysis of DHPS activity and content of free lysine in leaves was performed as described in Example 4. The same protocols were also used to determine the activity and the free lysine content in roots and tubers of the transgenic potato plants.

Leaves, roots and tubers from transgenic potato plants were screened for DHPS activity using the (O-ABA) assay as described for transgenic tobacco plants. In FIG. 8, DHPS activity in the transgenic potato plants (mean of triplicate determinations) is plotted relative to the average DHPS activity in control nontransformed Desiree plants, that was given the value of 1. As shown in this Figure, all transgenic plants possessed higher DHPS activity than the control plants. This activity was close to 60–40 fold higher than of control plants in leaves (A), roots (B) and tubers (C), respectively.

Figure 9:
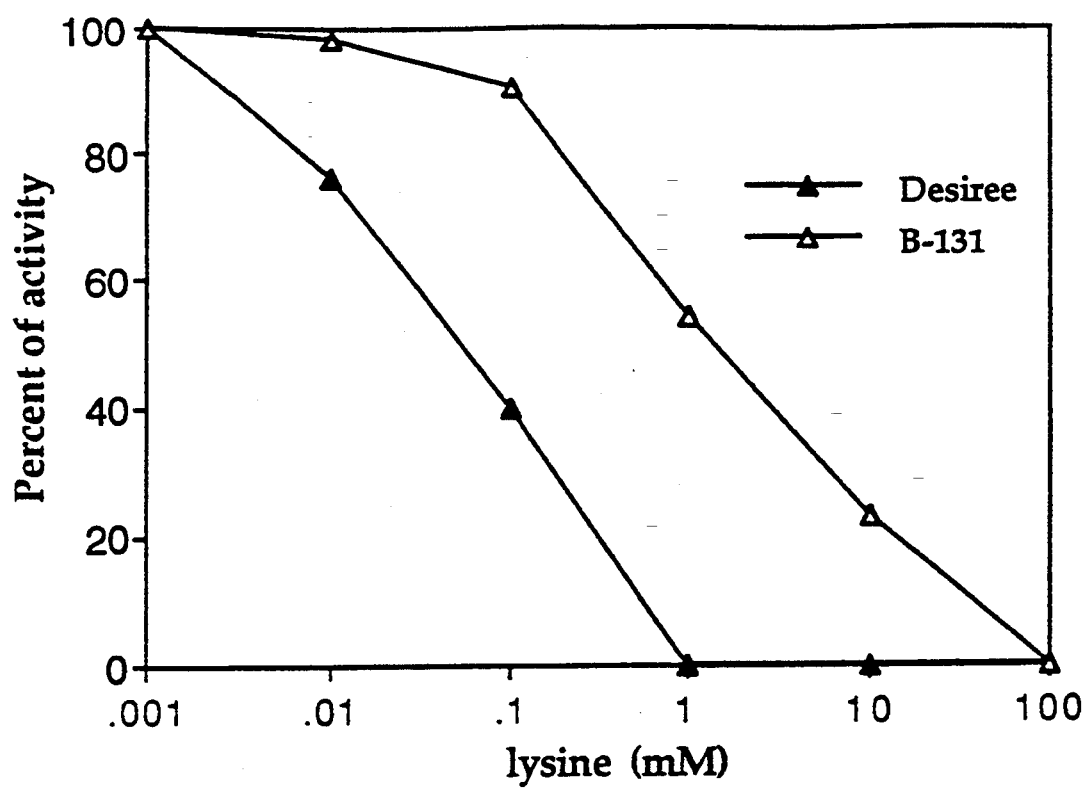
FIG. 9 illustrates the sensitivity of DHPS activity to lysine inhibition in the transgenic potato plants.

FIG. 9 illustrates the sensitivity of DHPS activity from the transgenic potato plants to lysine inhibition. DHPS activity was assayed in crude leaf extracts in the presence of increasing lysine concentrations. The relative activities at each lysine concentration (mean of triplicate determinations) are expressed as percentages of the DHPS activity in medium with no lysine added. As for tobacco, this assay proved that the elevated level of DHPS activity in transgenic plants clearly resulted from the expression of the E. coli enzyme in plant tissues.

Figure 10:
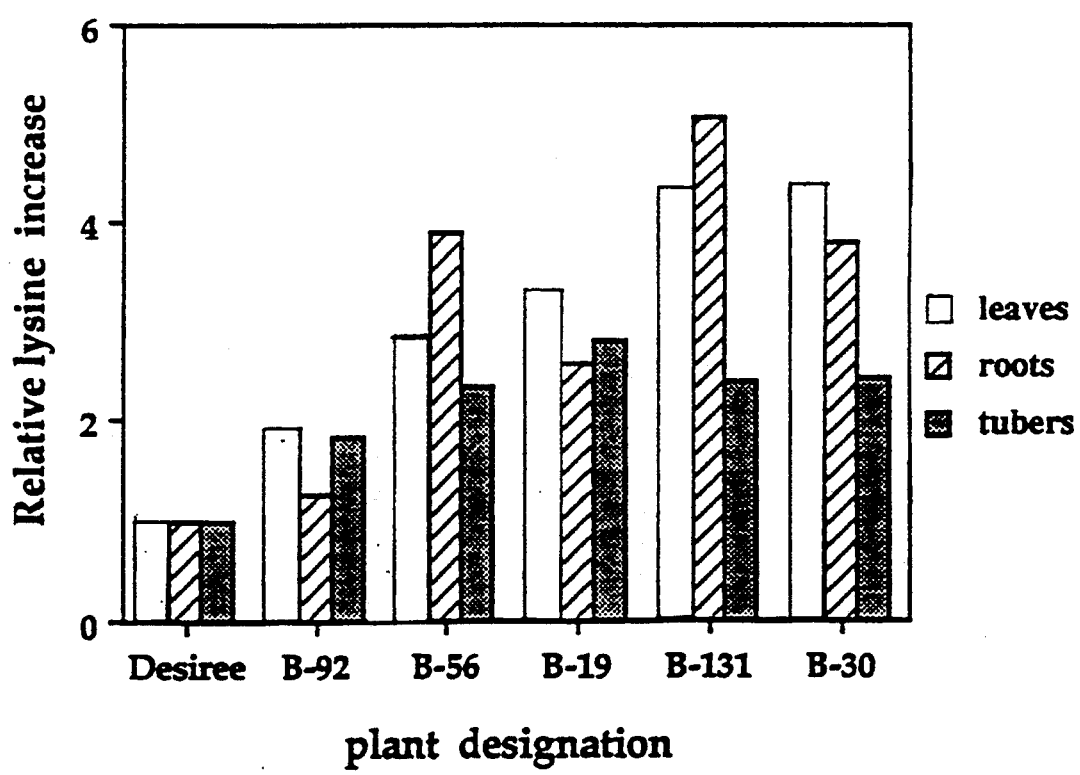
FIG. 10 shows the relative levels of free lysine in leaves, roots and tubers of the transgenic potato plants.

Total amino acids were extracted from leaves, roots and tubers of the transgenic potato plants using the same protocols as for transgenic tobacco plants. The level of free lysine in each transgenic genotype (mean of triplicate determinations) is plotted relative to the level of free lysine in the control nontransformed Desiree that was given the value of 1. FIG. 10 shows the relative increase in free lysine in leaves, roots and tubers of the transgenic potato plants.

Example 7

Plasmids for the construction of the chimeric gene for expression of AK

The construction of the plasmids Ca, Cb and Cc used for the construction of the chimeric gene as depicted in FIG. 12 was carried out as in Example 1.

Plasmid Cp was prepared as follows: a mutated E. coli lysC allele having the coding sequence for AK was cloned from a bacteriophage lambda library, made from the mutant, lysine overproducing E. coli strain TOC R21, by hybridization with DNA of the normal lysC gene (Cassan, M., et al., (1986) J. Biol. Chem. 261: 1052–1057). Plasmid Cp was obtained by cloning of a 1.3 kd KpnI-HaeIII fragment, containing the entire coding sequence of the mutant lysC allele except for 31 bp at the 5' end, into the KpnI-HincII sites of Bluescript SK+ plasmid (Stratagene). The coding DNA sequence of this mutated gene was not determined, but the coding DNA sequence of the wild-type lysC gene is shown in FIG. 11.

Example 8

Construction of the chimeric gene for expression of AK

The DNA vectors were constructed by standard procedures. Plasmid DNAs were purified by banding in CsCl-ethidium gradients (Maniatis, T., et al. (1982) Molecular Cloning: A Laboratory Manual, Cold Spring Harbor Laboratory). DNA restriction fragments were isolated by electrophoretic separation in agarose gels followed by purification with glass beads (using the Geneclean kit of bio 101). Restriction endonucleases (Boehringer, New England Biolabs), T4DNA ligase (Boehringer) and the large fragment of E. coli DNA polymerase (New England Biolabs) were used as recommended by the suppliers. E coli transformation was carried out with frozen competent bacteria (Maniatis, T., (1982) see above) using strain DH-5α (Clontech).

A schematic diagram of the construction of the chimeric gene containing the chloroplast transit peptide is shown in FIG. 12. The subcloning steps A to D were performed in E. coli.

Steps A and B were carried out as in Example 2.

In step (C), plasmid Cp was digested with KpnI (K) and EcoRI (RI) and the 1.3 kb DNA fragment containing the entire coding sequence of the mutant lysC allele (AK) except for 31 pb at the 5' end was isolated. In order to restore these 31 bp of DNA a double stranded synthetic oligonucleotide linker (L) was synthesized (sequence shown in FIG. 11b) that contained a KpnI site at its 3' end and a SphI (Sp) site at its 5' end. The isolated 1.3 kb DNA fragment and the synthetic oligonucleotide were ligated into the SphI and EcoRI sites of plasmid Ce to form plasmid Ck which contained the entire chimeric gene.

In step (D), plasmid Ck was digested with XbaI (X) and BamHI (B) and the 2.78 kb DNA fragment containing the chimeric gene was isolated and ligated into the XbaI and BglII (Bg) sites of plasmid pGA492 to create plasmid Co.

To construct the chimeric gene without the DNA sequence coding for the transit peptide, step B was omitted, so that in step C plasmid Cd was utilized instead of plasmid Ce.

Example 9

Transformation of tobacco plants

For plant transformation the Ti plasmid with the chimeric gene was immobilized into the *Agrobacterium tumefaciens* strain LBA4404 by the triparental mating protocol (Ditta, G., et al. (1980) Proc. Natl. Acad. Sci. USA 77: 7347) using the E. coli bacterial strain pRK2013 which contained mating genes on a plasmid. The three bacteria i.e. the E. coli with the chimeric gene, the E. coli strain pRK2013 and the *Agrobacterium tumefaciens* strain LBA4404 were mixed and allowed to grow overnight on an antibiotic free rich medium. A. tumefaciens LBS4404 containing the Ti plasmid with the chimeric gene was then selected on rich medium containing 100 μg/ml rifampicin, 25 μg/ml kanamycin and 5 μg/ml tetracycline, and utilized to infect tobacco leaf disks. Transgenic plants were regenerated on kanamycin and carbenicillin containing media as described previously (Horsch, R. B., et al. (1985) Science 227: 1229–1231).

Example 10

Analysis of AK activity and content of free threonine in the transgenic plants

Two types of transgenic plants were utilized. The chloroplastic type contained the chimeric AK gene described in FIG. 12. The cytoplasmic type contained the chimeric gene without the DNA sequence coding for the transit peptide. In the transgenic plants containing the cytoplasmic type chimeric gene the mutated E. coli AK was apparently expressed in the cytoplasm, and in the transgenic plants containing the chloroplastic type chimeric gene the mutated E. coli AK was apparently expressed in the chloroplast.

Transgenic plants were screened for an elevated AK activity. AK activity was assayed in crude extracts from leaves of transgenic plants by the method of Black and Wright (Black, S., et al. (1955) J. Biol. Chem. 213: 27–38). Leaves from axenic tobacco plants grown on Nitsch minimal medium (Nitsch, J. P. (1969) Phytomorphology 19: 389–404) in Magenta boxes for about one month were homogenized with a mortar and pestle in an equal volume of cold 20 mM potassium phosphate buffer pH 7.0 containing 30 mM β-mercaptoethanol, 0.1 mM L-lysine, 0.1 mM L-threonine, 1 mM phenylmethylsulfonilfluoride and 0.5 mM leupeptin. Following 5 min centrifugation (16,000 .g, 4° C.) the supernatant was collected and its protein concentration was determined by the method of Bradford (Bradford, M. M. (1976) Anal. Biochem. 72: 248–254). Equal amounts of protein were then tested for AK activity. The assay mixture contained in a final volume of 0.25 ml, 300 μg protein, 100 mM tris-HCl pH 8.0, 200 mM $NH_2OH$ neutralized prior to use with KOH, 10 mM ATP, 5 mM $MgCl_2$, and 30 mM L-aspartate, using as a control an assay mixture which contained all the ingredients except L-aspartate. The reaction mixture was stopped by addition of 0.25 ml of a 1:1:1 mixture of 10% $FeCl_3$ in 0.1M HCl, 3M HCl and 12% TCA, centrifuged and the optical absorbance of the supernatant at 490 nm was measured.

In FIG. 13, the AK activity in the leaves of each transgenic genotype (average of three measurements for each transgenic genotype) is plotted relative to the average AK activity in the leaves of seven control plants (Con.) which was given the value of 1. (E-6 to E-36) Transgenic genotypes expressing the chloroplastic-type AK; (C-8 and C-21) Transgenic genotypes expressing the cytoplasmic-type AK. The transgenic plant E-26 contained the highest AK activity which was close to 17 fold higher than that of control plants.

FIG. 14 shows the sensitivity of the AK activity in the leaves of the transgenic plants to inhibition by lysine and threonine. AK activity was measured in crude extracts prepared from tobacco leaves as above except that 10 mM lysine, threonine or both amino acids were present in the reaction mixture as indicated on the right. The Y axis represents the percent activity relative to the control with no lysine or threonine added to the reaction mixture. (Con.) nontransformed plant; (E-6) transgenic plant expressing the chloroplastic-type AK. Lysine and threonine when present alone inhibited 14 and 70%, respectively, of nontransformed tobacco leaf AK activity, and when present together inhibited more than 80% of this activity. In contrast, the AK activity in the transgenic plant E-6 containing the chloroplast type gene, was completely resistant to inhibition by either 10 mM lysine or 10 mM threonine; or a mixture of both. Therefore, the elevated levels of AK activity in the leaves of the transgenic plants result from the expression of the E. coli mutated, desensitized enzyme in them.

Figure 15:
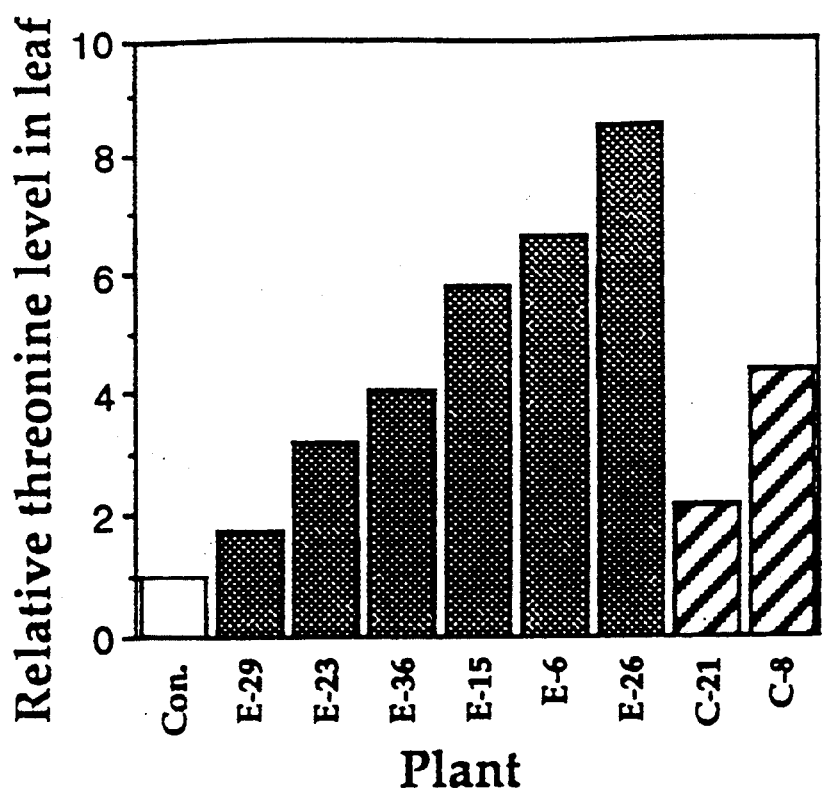
FIG. 15 shows the relative levels of free threonine in leaves of the transgenic tobacco plants.
Figure 16:
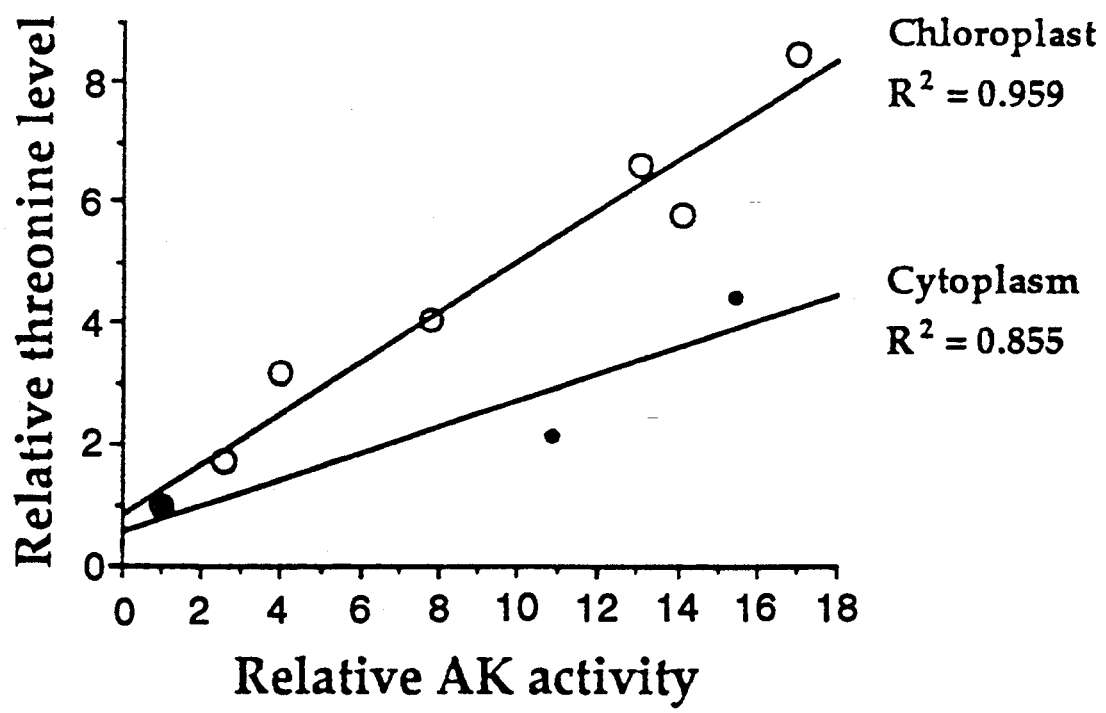
FIG. 16 shows the correlation between AK activity and threonine level in the leaves of the transgenic tobacco plants.

The content of free threonine in leaves of the transgenic plants was next measured. The content of free threonine, normalized to free threonine in control nontransformed plants is shown in FIG. 15. The increase in the relative content of free threonine in the leaves of the selected transgenic plants correlated well with the level of AK activity in the leaves of these plants (FIG. 16). Plants containing either the chloroplastic type chimeric gene or the cytoplasmic type chimeric gene showed increased threonine level (FIGS. 15 and 16). Yet, threonine production was higher in plants expressing an apparent chloroplastic type enzyme than in plants expressing an apparent cytoplasmic type enzyme that have the same AK activity (FIG. 16).

FIG. 15 shows the relative levels of free threonine in leaves of transgenic plants. Leaves (100 mg FW) from axenic tobacco plants, grown for about one month on Nitsch minimal medium in Magenta boxes, were harvested, their free amino acids were immediately extracted as described by Bieleski (Bieleski, R. L., et al. (1966) Anal. Biochem. 17: 278–293) and the concentration of free amino acids as well as the amino acid composition were determined. The level of free threonine in the leaves of each transgenic genotype (average of three measurements for each transgenic genotype) was plotted relative to the average level of free threonine in seven control plants (Con.) which was given the value of 1. (E-6 to E-36) Transgenic plants expressing the chloroplastic-type AK; (C-8 and C-21 ) Transgenic plants expressing the cytoplasmic-type AK.

FIG. 16 shows the correlation between AK activity and threonine level in the leaves of the transgenic plants. The relative threonine level of each transgenic genotype, that was represented in FIG. 15, is plotted against the relative AK activity of the same transgenic genotype, that was represented in FIG. 13.

Figure 17:
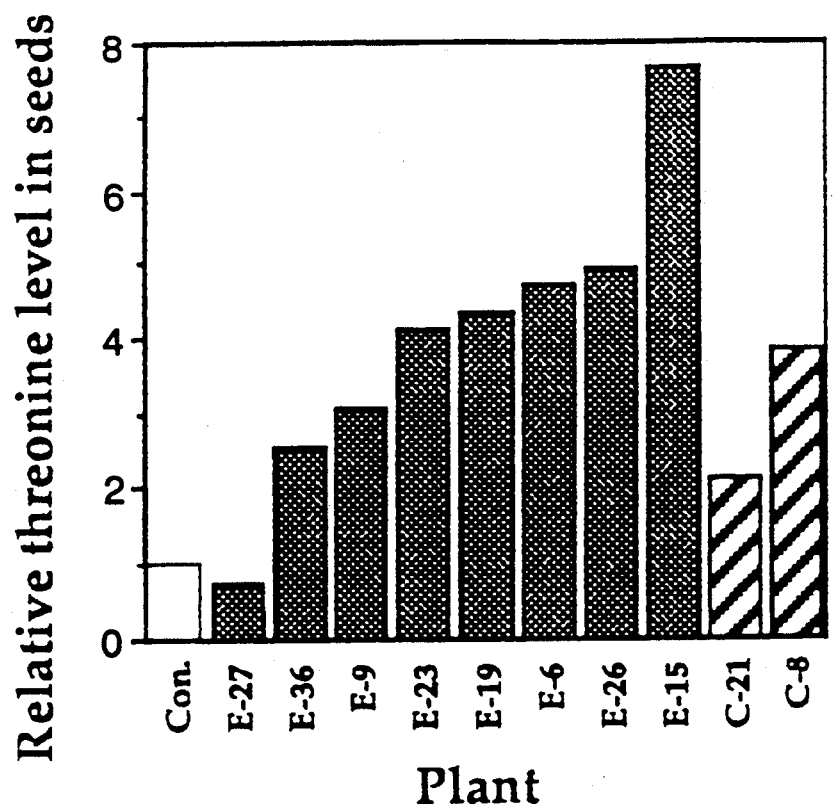
FIG. 17 shows the relative levels of free threonine in seeds of the transgenic tobacco plants.

The content of free threonine in seeds of the transgenic plants was next measured. Seeds (100 mg) were harvested from tobacco plants grown in the greenhouse and their free amino acids were immediately extracted and subjected to amino acid composition analysis. FIG. 17 shows the relative levels of free threonine in seeds of selected transgenic plants. The content of free threonine, normalized to free threonine in the seeds of control nontransformed plants is shown in the Figure. The level of free threonine in each transgenic genotype (average of three measurements for each transgenic genotype) is plotted relative to the average level of free threonine in seven control plants (Con), which was given the value of 1. (E-6 to E-36) Transgenic plants expressing the AK in the chloroplast; (C-8 and C-21) Transgenic plants expressing the AK in the cytoplasm. The relative increase in the content of free threonine in the seeds of the selected transgenic plants does not necessarily correlate with the relative increase in the content of free threonine in the leaves of these plants. This difference in the relative expression of the chimeric gene in various tissues is due to the effect of the site of its insertion into the plant genome. Plants containing either the chloroplastic type chimeric gene or the cytoplasmic type chimeric gene showed increased threonine level in the seeds.

Example 11

Crossing between transgenic plants expressing the E. coli AK and DHPS

Transgenic tobacco plants expressing the chloroplastic type E. coli DHPS were crossed with transgenic tobacco plants expressing the E. coli AK. The progeny produced more lysine than the parental DHPS and AK expressing plants and also overproduced lysine.

Figure 23:
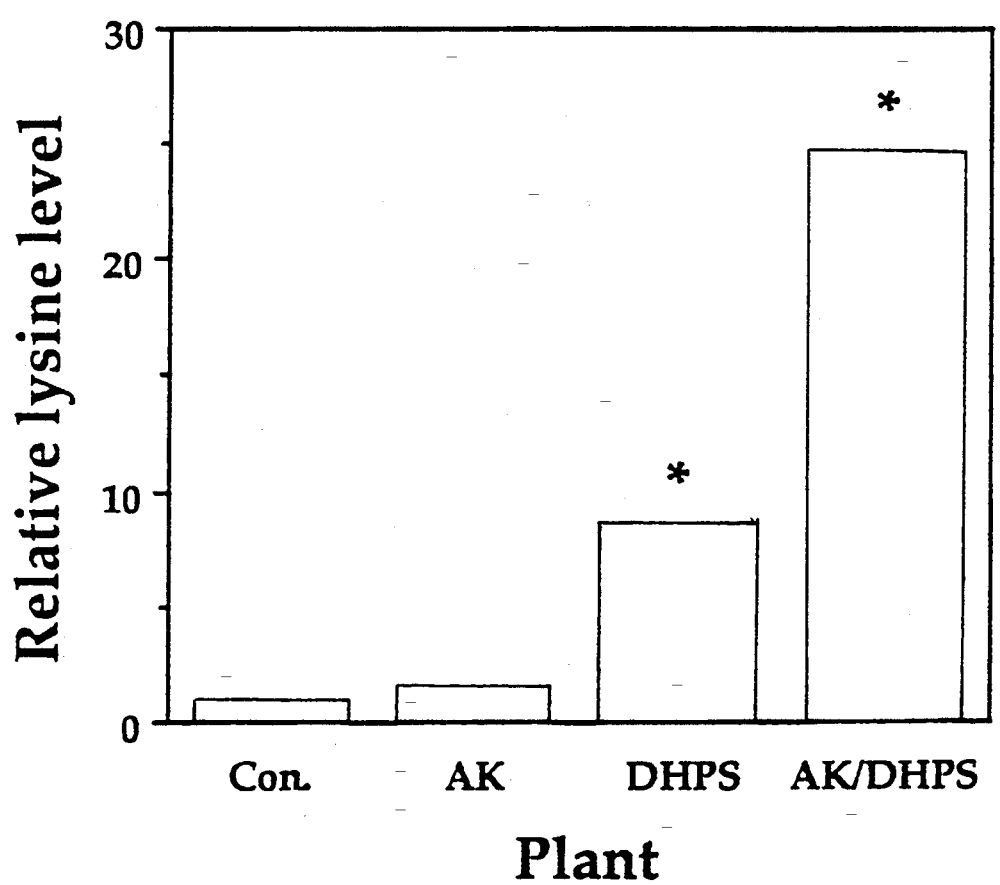
FIG. 23 shows the relative levels of free lysine in leaves of transgenic tobacco plants expressing the *E. coli* AK and DHPS and $F_1$ hybrids resulting from crossing thereof.

FIG. 23 shows the relative levels of free lysine in leaves of heterozygous transgenic plants expressing the E. coli AK, the E. coli DHPS and $F_1$ hybrids resulting from cross of the two plants. Leaves (100 mg FW) from axenic tobacco plants, grown for about one month on Nitsch minimal medium in Magenta boxes, were harvested and their free amino acids were immediately extracted and subjected to amino acid composition analysis. The level of free lysine in the parents and the $F_1$ hybrid (average of three measurements for each transgenic genotype) is plotted relative to the average level of free lysine in control nontransformed plants (Con.), which was given the value of 1. (AK) transgenic plants expressing the bacterial AK; (DHPS) transgenic plants expressing the bacterial DHPS; (AK/DHPS)$F_1$ hybrids. An asterisk on top of the bar indicates a significant difference from the control at the 0.05 level. As shown, the parental plants expressing AK showed almost no increase in lysine, the parental plant expressing DHPS exhibited a 9 fold increase in lysine synthesis and the progeny of the cross exhibited a increase in lysine synthesis. The threonine level in these progeny, although being lower compared to the parental plant expressing AK, was higher than that of the control plant by about 3 to 5 fold. Thus, the progeny of the cross expressing the E. coli AK and DHPS together overproduced both lysine and threonine.

Example 12

Analysis of AK activity and content of free threonine in transgenic potato plants The basic transformation procedure was similar to the protocol used to transform potato tuber disks with the DHPS gene as described in Example 5.

Figure 18:
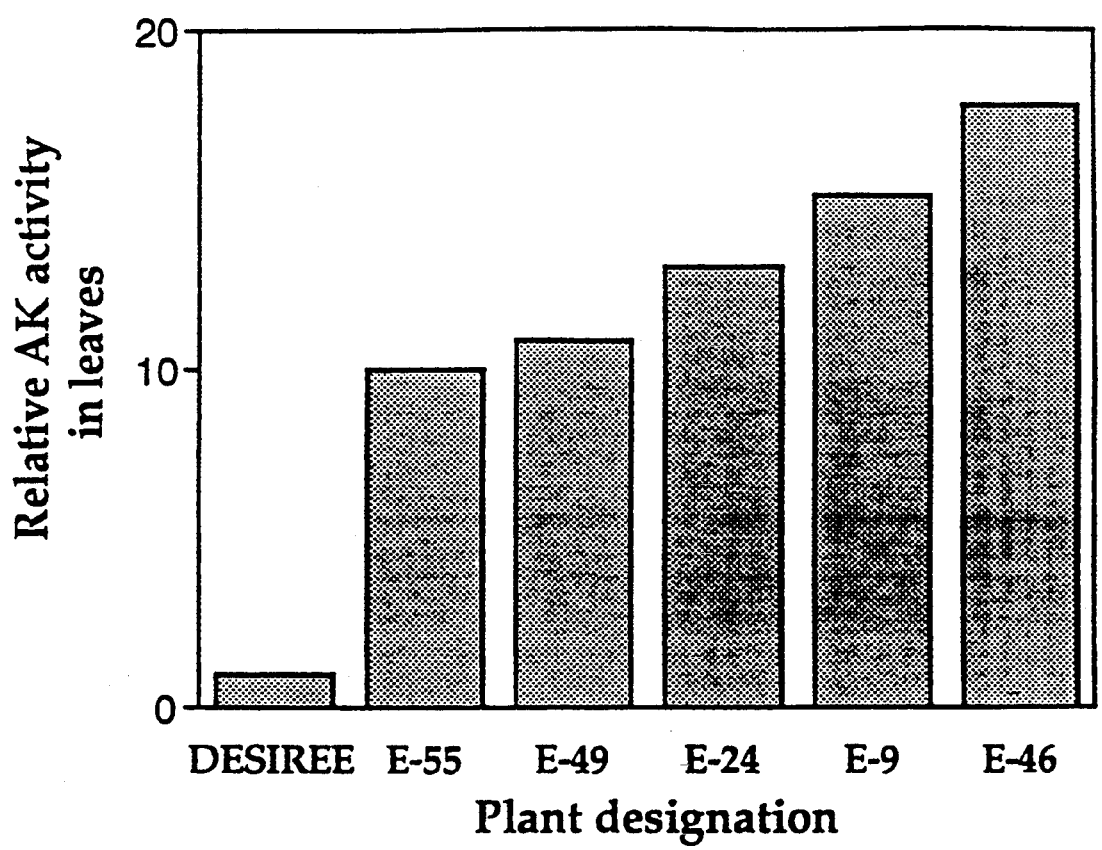
FIG. 18 shows the relative AK activity in leaves of transgenic potato plants.
Figure 19:
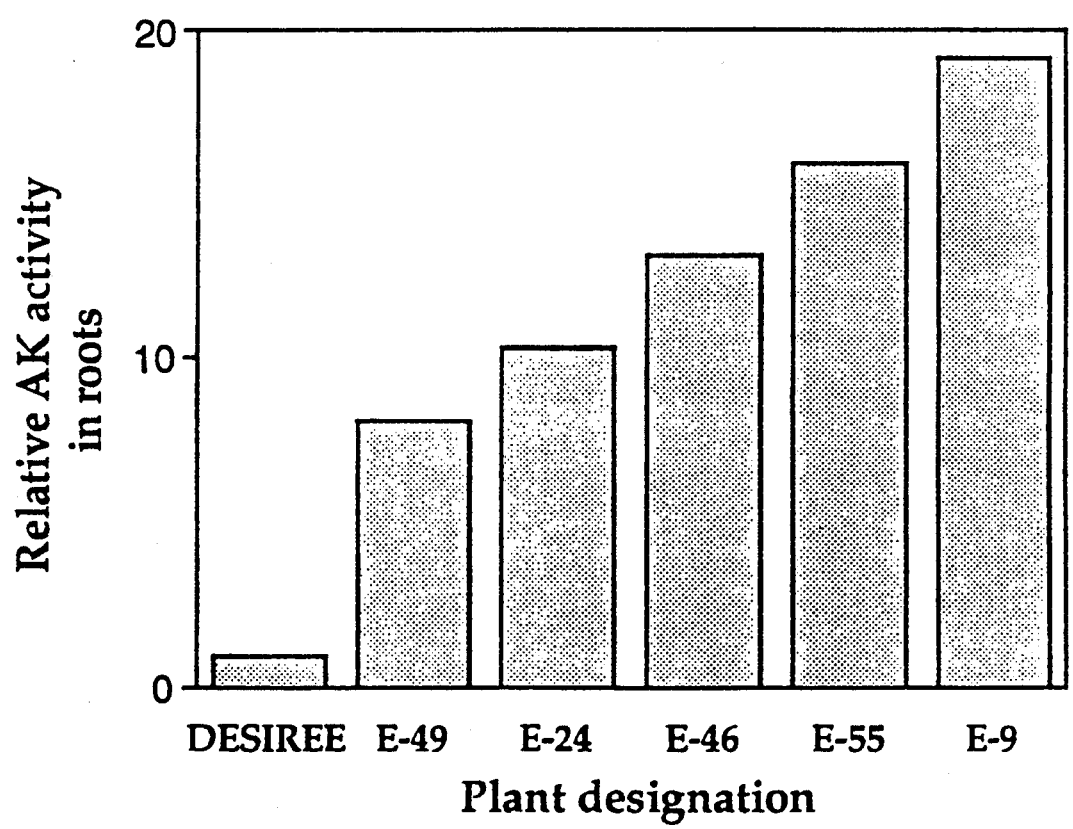
FIG. 19 shows the relative AK activity in roots of transgenic potato plants.

Leaves and roots from transgenic potato S. tuberosum cv. "Desiree" plants were screened for AK activity using the same protocols described above for tobacco AK transgenic plants. In FIGS. 18 and 19, relative AK activity in leaves (FIG. 18) and roots (FIG. 19) of transgenic potato plants (mean of triplicate determinations) is plotted relatively to the mean AK activity of control nontransformed plants (Desiree), that was given the value of 1. As shown, all transgenic plants (E9 to E55-) possessed higher AK activity than the control plants. This activity was almost 10–20 fold higher than of control plants in leaves (FIG. 18) and roots (FIG. 19).

Figure 20:
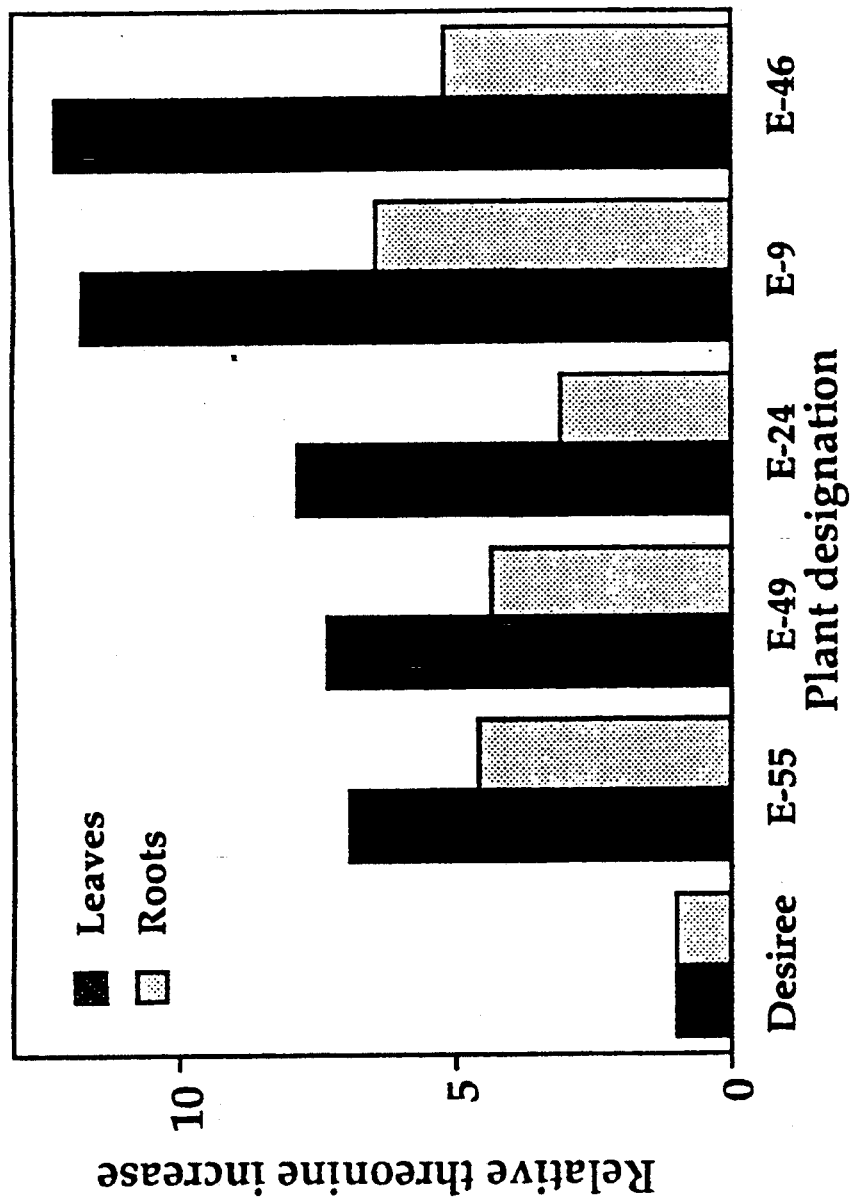
FIG. 20 shows the relative levels of free threonine in leaves and roots of the transgenic potato plants.

Total amino acids were extracted from leaves and roots of the transgenic potato plants using the same protocols as for transgenic tobacco plants. FIG. 20 shows the relative increase in free threonine in leaves and roots of transgenic potato plants. The level of free threonine in each transgenic plant as well as in nontransformed control plant is plotted relatively to the level of free threonine in the control plants, which was given the value of 1.

Example 13

Co-transformation of the potato plants with chimeric genes comprising the DHPS and AK genes In a first experiment, tubers derived from transgenic potato plants already containing the DHPS gene were used as starting materials.

Tubers of S. tuberosum cv. "Desiree" lines B-19, B-30 and B-131 (expressing the bacterial DHSP gene) were surface-sterilized in 1% sodium hypochlorite for 20 min and then washed 3 times in sterile distilled water. The transformation procedure of Sheermann and Bevan (1988) with some modifications was followed. Three mm thick tuber disks were incubated for 20 min in overnight cultures of Agrobacterium tumefaciens containing the AK construct. After blotting on sterile paper the disks were cultured in solidified (1% agar) MS medium supplemented with 2 mg/l zeatin riboside and 1 mg/l indole-3-aspartic-acid. After 48 h of co-cultivation the disks were transferred to the same medium but with the addition of 500 µg/ml carbenicillin and 2 mM of both lysine and threonine. This is a mild selection pressure favoring the regeneration of plants expressing both the DHPS and AK genes. After about one month of culture (24° C., 40 µE $m^{-2}$ $s^{-1}$ light fluence), shoots were regenerated. These were further rooted on solidified (0.8% agar) Nitsch medium supplemented with 5 mM threonine, 0.15 mM AEC, 1 mg/l indole-3-butyric acid (IBA) and 250 µg/ml carbenicillin. Regenerated shoots that rooted in the presence of both threonine and AEC were transferred to the greenhouse for further observations, propagation and analyses.

In another experiment, tubers derived from transgenic potato plants already containing the AK gene were used as starting material.

Tubers of S. tuberosum cv. "Desiree" lines E-9, E-24 and E-46 (expressing the bacterial AK gene) were treated as described above for the plants expressing the DHPS gene, but the tuber disks were incubated with culture of Agrobacterium tumefaciens containing the DHPS construct. Regeneration and rooting took place on Nitsch medium supplemented with the same phytohormones but with 0.3 mM or 0.15 mM AEC for regeneration and rooting respectively.

Example 14

Resistance of transgenic tobacco plants to aminoethylcysteine (AEC)

To test whether the transgenic tobacco plants expressing the E. coli DHPS gene were more resistant to the lysine analog AEC compared to control nontransformed plants, shoots from control plants (FIG. 21, left) and from transgenic tobacco plant B-7 (FIG. 21, right) were dipped in MS medium containing 2 mg/l kinetin, 0.8 mg/l IAA and either 0, 0.1, 0.15 or 0.2 mM AEC. As shown in FIG. 21, the transgenic plant clearly grows better than the control in medium containing 0.1 and 0.15 mM AEC.

Example 15

Figure 22A:
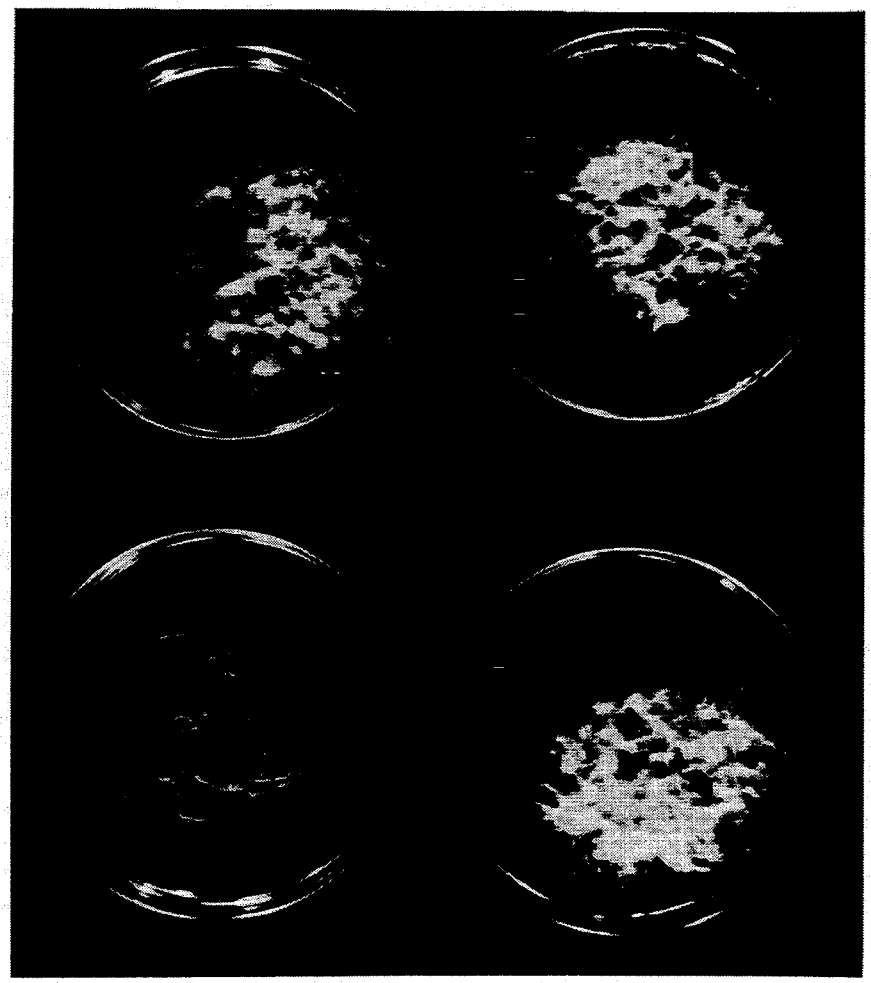
FIGS. 22A and 22B illustrate the phytotoxicity of a mixture of lysine and threonine to transgenic and non-transgenic plants.

Phytotoxicity of a mixture of lysine and threonine to transgenic and nontransgenic plants Root sections derived from wild type "Desiree" (W.T.) and transgenic potato plants expressing the AK gene were cultivated in MS medium supplemented with 1 mg/l IBA with and without 2 mM of both lysine and threonine. The fresh weight increase of the wild type was similar to the fresh weight increase in the transgenic potato plant in control medium without lysine and threonine (FIG. 22A upper row). When cultured in the presence of 2 mM lysine and threonine, the growth of the wild type potato was totally inhibited while no significant decrease was observed in the fresh weight increase of roots derived from the plant expressing the AK gene (FIG. 22A, lower row).

Figure 22B:
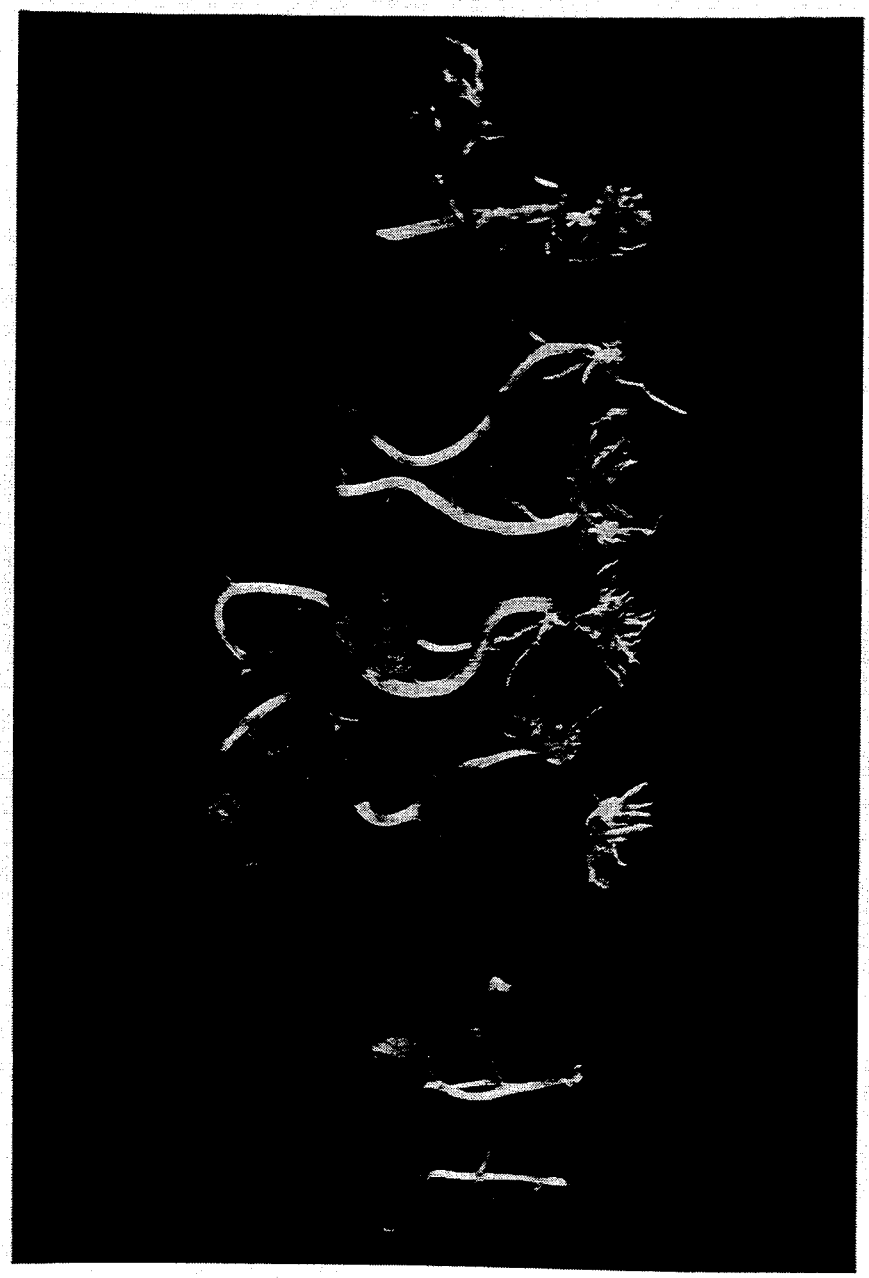

Transgenic shoots (only AK) that regenerated and rooted in the presence of kanamycin were also rooted on a medium supplemented with 1 mg/l IBA and 2 mM of both lysine and threonine. Control wild type shoots hardly rooted (FIG. 22B, left) while transgenic potato shoots expressing the E. coli AK gene exhibited profuse rooting (FIG. 22B, right).

We claim:

1. A transgenic plant whose cells contain (i) a recombinant DNA molecule which comprises (a) the sequence of the lysC gene from *E. coli* encoding an enzyme having aspartate kinase (AK) activity, and (b) sequences capable of enabling the expression of the enzyme in a plant cell, such expression causing the subsequent production of high levels of threonine therein, and (ii) a further recombinant DNA molecule which comprises (a) the sequence of the dapA gene from *E. Coli* encoding an enzyme having dihydrodipicolinate synthase (DHPS) activity, and (b) sequences capable of enabling the expression of the enzyme in a plant cell which comprise (1) a plant promoter, (2) a plant polyadenylation and termination sequence and (3) a sequence encoding a chloroplast transit peptide, said chloroplast transit peptide sequence being fused to the 5'-end of the sequence of the dapA gene from *E. coli* encoding an enzyme having dihydrodipicolinate synthase (DHPS) activity.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TATTTTTACA ACAATTACCA ACAACAACAA ACAACAAACA ACATTACAAT TACTATTTAC      60
```

( 2 ) INFORMATION FOR SEQ ID NO:2:

( i ) SEQUENCE CHARACTERISTICS:
        ( A ) LENGTH: 184 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
TCTAGAAAAA TGGCTTCTAT GATATCCTCT TCCGCTGTGA CAACAGTCAG CCGTGCCTCT      60
AGGGGGCAAT CCGCCGCAGT GGCTCCATTC GGCGGCCTCA ATCCATGAC TGGATTCCCA      120
GTGAAGAAGG TCAACACTGA CATTACTTCC ATTACAAGCA ATGGTGGAAG AGTAAAGTGC      180
ATGC                                                                   184
```

( 2 ) INFORMATION FOR SEQ ID NO:3:

( i ) SEQUENCE CHARACTERISTICS:
        ( A ) LENGTH: 886 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
ATGTTCACGG GAAGTATTGT CGCGATTGTT ACTCCGATGG ATGAAAAGG  TAATGTCTGT      60
CGGGCTAGCT TGAAAAAACT GATTGATTAT CATGTCGCCA GCGGTACTTC GGCGATCGTT     120
TCTGTTGGCA CCACTGGCGA GTCCGCTACC TTAAATCATG ACGAACATGC TGATGTGGTG     180
ATGATGACGC TGGATCTGGC TGATGGGCGC ATTCCGGTAA TTGCCGGGAC CGGCGCTAAC     240
GCTACTGCGG AAGCCATTAG CCTGACGCAG CGCTTCAATG ACAGTGGTAT CGTCGGCTGC     300
CTGACGGTAA CCCCTTACTA CAATCGTCCG TCGCAAGAAG GTTTGTATCA GCATTTCAAA     360
GCCATCGCTG AGCATACTGA CCTGCCGCAA ATTCTGTATA ATGTGCCGTC CCGTACTGGC     420
TGCGATCTGC TCCCGGAAAC GGTGGGCCGT CTGGCGAAAG TAAAAAATAT TATCGGAATC     480
AAAGAGGCAA CAGGGAACTT AACGCGTGTA AACCAGATCA AAGAGCTGGT TCAGATGAT     540
TTTGTTCTGC TGAGCGGCGA TGATGCGAGC GCGCTGGACT TCATGCAATT GGGCGGTCAT     600
GGGGTTATTT CCGTTACGAC TAACGTCGCA GCGCGTGATA TGGCCCAGAT GTGCAAACTG     660
GCAGCAGAAG AACATTTTGC CGAGGCACGC GTTATTAATC AGCGTCTGAT GCCATTACAC     720
AACAAACTAT TTGTCGAACC CAATCCAATC CCGGTGAAAT GGGCATGTAA GGAACTGGGT     780
CTTGTGGCGA CCGATACGCT GCGCCTGCCA ATGACACCAA TCACCGACAG TGGTCGTGAG     840
```

| ACGGTCAGAG | CGGCGCTTAA | GCATGCCGGT | TTGCTGTAAA | GTTTAG | 886 |

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

| TTCACGGGAA | GTATTGTCG | | | | 19 |

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

| GTACAAGTGC | CCTTCATAAC | AGC | | | 23 |

(2) INFORMATION FOR SEQ ID NO:6:

(i) SEQUENCE CHARACTERISTICS:
        (A) LENGTH: 194 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

| CAGCTGCTTT | AATGAGATAT | GCGAGACGCC | TATGATCGCA | TGATATTTGC | TTTCAATTCT | 60 |
| GTTGTGCACG | TTGTAAAAAA | CCTGAGCATG | TGTAGCTCAG | ATCCTTACCG | CCGGTTTCGG | 120 |
| TTCATTCTAA | TGAATATATC | ACCCGTTACT | ATCGTATTTT | TATGAATAAT | ATTCTCCGTT | 180 |
| CAATTTACTG | ATTG | | | | | 194 |

(2) INFORMATION FOR SEQ ID NO:7:

(i) SEQUENCE CHARACTERISTICS:
        (A) LENGTH: 1350 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

| ATGTCTGAAA | TTGTTGTCTC | CAAATTTGGC | GGTACCAGCG | TAGCCGATTT | TGACGCCATG | 60 |
| AACCGCAGCG | CTGATATTGT | GCTTTCTGAT | GCCAACGTGC | GTTTAGTTGT | CCTCTCGGCT | 120 |
| TCTGCTGGTA | TCACTAATCT | GCTGGTCGCT | TTAGCTGAAG | GACTGGAACC | TTGCGAGCGA | 180 |
| TTCGAAAAAC | TCGACGCTAT | CCGCAACATC | CAGTTTGCCA | TTCTGGAACG | TCTGCGTTAC | 240 |
| CCGAACGTTA | TCCGTGAAGA | GATTGAACGT | CTGCTGGAGA | ACATTACTGT | TCTGGCAGAA | 300 |
| GCGGCGGCGC | TGGCAACGTC | TCCGGCGCTG | ACAGATGAGC | TGGTCAGCCA | CGGCGAGCTG | 360 |
| ATGTCGACCC | TGCTGTTTGT | TGAGATCCTG | CGCGAACGCG | ATGTTCAGGC | ACAGTGGTTT | 420 |
| GATGTGCGTA | AAGTGATGCG | TACCAACGAC | CGATTTGGTC | GTGCAGAGCC | AGATATAGCC | 480 |

| | | | | | | |
|---|---|---|---|---|---|---|
| GCGCTGGCGG | AACTGGCCGC | GCTGCAGCTG | CTCCCACGTC | TCAATGAAGG | CTTAGTGATC | 540 |
| ACCCAGGGAT | TTATCGGTAG | CGAAAATAAA | GGTCGTACAA | CGACGCTTGG | CCGTGGAGGC | 600 |
| AGCGATTATA | CGGCAGCCTT | GCTGGCGGAG | GCTTTACACG | CATCTCGTGT | TGATATCTGG | 660 |
| ACCGACGTCC | CGGGCATCTA | CACCACCGAT | CCACGCGTAG | TTTCCGCAGC | AAAACGCATT | 720 |
| GATGAAATCG | CGTTTGCCGA | AGCGGCAGAG | ATGGCAACTT | TTGGTGCAAA | AGTACTGCAT | 780 |
| CCGGCAACGT | TGCTACCCGC | AGTACGCAGC | GATATCCCGG | TCTTTGTCGG | CTCCAGCAAA | 840 |
| GACCCACGCG | CAGGTGGTAC | GCTGGTGTGC | AATAAAACTG | AAAATCCGCC | GCTGTTCCGC | 900 |
| GCTCTGGCGC | TTCGTCGCAA | TCAGACTCTG | CTCACTTTGC | ACAGCCTGAA | TATGCTGCAT | 960 |
| TCTCGCGGTT | TCCTCGCGGA | AGTTTTCGGC | ATCCTCGCGC | GGCATAATAT | TTCGGTAGAC | 1020 |
| TTAATCACCA | CGTCAGAAGT | GAGCGTGGCA | TTAACCCTTG | ATACCACCGG | TTCAACCTCC | 1080 |
| ACTGGCGATA | CGTTGCTGAC | ACAATCTCTG | CTGATGGAGC | TTTCCGCACT | GTGTCGGGTG | 1140 |
| GAGGTGGAAG | AAGGTCTGGC | GCTGGTCGCG | TTGATTGGCA | ATGACCTGTC | AAAAGCGTGC | 1200 |
| GCCGTTGGCA | AAGAGGTATT | CGGCGTACTG | GAACCGTTCA | ACATTCGCAT | GATTTGTTAT | 1260 |
| GGCGCATCCA | GCCATAACCT | GTGCTTCCTG | GTGCCCGGCG | AAGATGCCGA | GCAGGTGGTG | 1320 |
| CAAAAACTGC | ATAGTAATTT | GTTTGAGTAA | | | | 1350 |

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TCTGAAATTG TTGTCTCCAA ATTTGGCGGT AC                                32

( 2 ) INFORMATION FOR SEQ ID NO:9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GTACAGACTT TAACAACAGA GGTTTAAACC GC                                32